United States Patent
Bae et al.

(10) Patent No.: US 12,291,500 B2
(45) Date of Patent: *May 6, 2025

(54) CARBAZOLE DERIVATIVE AND ORGANIC LIGHT EMITTING ELEMENT USING SAME

(71) Applicant: LG Chem, Ltd., Seoul (KR)

(72) Inventors: Jaesoon Bae, Daejeon (KR); Jinseck Kim, Daejeon (KR); Sungkyoung Kang, Daejeon (KR); Chung Whan Lee, Daejeon (KR); Jaechol Lee, Daejeon (KR); Seokhee Yoon, Daejeon (KR); Donggu Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 540 days.

This patent is subject to a terminal disclaimer.

(21) Appl. No.: 16/093,799

(22) PCT Filed: Feb. 13, 2017

(86) PCT No.: PCT/KR2017/001555
§ 371 (c)(1),
(2) Date: Oct. 15, 2018

(87) PCT Pub. No.: WO2017/183806
PCT Pub. Date: Oct. 26, 2017

(65) Prior Publication Data
US 2019/0127327 A1 May 2, 2019

(30) Foreign Application Priority Data
Apr. 22, 2016 (KR) ........................ 10-2016-0049481

(51) Int. Cl.
*C07D 209/88* (2006.01)
*C07C 211/54* (2006.01)
(Continued)

(52) U.S. Cl.
CPC .......... *C07D 209/88* (2013.01); *C07C 211/54* (2013.01); *C07D 209/82* (2013.01);
(Continued)

(58) Field of Classification Search
CPC ...... H10K 50/11; H10K 50/15; H10K 50/155; H10K 50/16; H10K 50/17; H10K 85/111;
(Continued)

(56) References Cited

U.S. PATENT DOCUMENTS 10,954,218 B2 * 3/2021 Bae ...................... C07D 403/12
2007/0029927 A1 * 2/2007 Kawamura ................. 313/504
(Continued)

FOREIGN PATENT DOCUMENTS

JP   2010195708 A   9/2010
JP   2012015472 A   1/2012
(Continued)

OTHER PUBLICATIONS

Machine translated English version, JP 2012/111719, Tomoki Kato, Jun. 14, 2012 (Year: 2012).*
(Continued)

*Primary Examiner* — Seokmin Jeon
(74) *Attorney, Agent, or Firm* — Lerner David LLP

(57) ABSTRACT

The present specification relates to a carbazole derivative of Chemical Formula 1, a coating composition including the carbazole derivative, an organic light emitting device using the same and a method for manufacturing the same.

8 Claims, 3 Drawing Sheets

(51) Int. Cl.
| | |
|---|---|
| *C07D 209/82* | (2006.01) |
| *C07D 401/14* | (2006.01) |
| *C07D 403/12* | (2006.01) |
| *C09D 4/00* | (2006.01) |
| *C09K 11/06* | (2006.01) |
| *H10K 50/11* | (2023.01) |
| *H10K 50/15* | (2023.01) |
| *H10K 50/155* | (2023.01) |
| *H10K 50/16* | (2023.01) |
| *H10K 50/17* | (2023.01) |
| *H10K 71/00* | (2023.01) |
| *H10K 85/10* | (2023.01) |
| *H10K 85/60* | (2023.01) |

(52) U.S. Cl.
CPC ......... *C07D 401/14* (2013.01); *C07D 403/12* (2013.01); *C09D 4/00* (2013.01); *C09K 11/06* (2013.01); *H10K 50/11* (2023.02); *H10K 50/17* (2023.02); *H10K 71/00* (2023.02); *H10K 85/111* (2023.02); *H10K 85/626* (2023.02); *H10K 85/631* (2023.02); *H10K 85/633* (2023.02); *H10K 85/636* (2023.02); *H10K 85/6572* (2023.02); *H10K 50/15* (2023.02); *H10K 50/155* (2023.02); *H10K 50/16* (2023.02)

(58) Field of Classification Search
CPC .. H10K 85/626; H10K 85/631; H10K 85/633; H10K 85/636; H10K 85/6572; H10K 71/00; H01L 51/0035; H01L 51/0058; H01L 51/0059; H01L 51/006; H01L 51/0061; H01L 51/0072; H01L 51/5012; H01L 51/5056; H01L 51/506; H01L 51/5072; H01L 51/5088; H01L 51/56; C07C 211/54; C07D 209/82; C07D 209/88; C07D 401/14; C07D 403/12; C09D 4/00; C09K 11/06; C09K 2211/1014; C09K 2211/1029
See application file for complete search history.

(56) References Cited

U.S. PATENT DOCUMENTS

| | | | | |
|---|---|---|---|---|
| 2010/0145067 | A1* | 6/2010 | Yokota | ............................ 548/442 |
| 2012/0001127 | A1 | 1/2012 | Brown et al. | |
| 2015/0084020 | A1 | 3/2015 | Nagao et al. | |
| 2016/0028013 | A1 | 1/2016 | Jou et al. | |
| 2016/0301011 | A1* | 10/2016 | Nakaie | ............... H01L 51/0059 |
| 2018/0354933 | A1 | 12/2018 | Bae et al. | |
| 2020/0020873 | A1* | 1/2020 | Lee | ..................... H01L 51/5092 |

FOREIGN PATENT DOCUMENTS

| | | |
|---|---|---|
| JP | 2012111719 A | 6/2012 |
| JP | 2013536570 A | 9/2013 |
| JP | 2019503988 A | 2/2019 |
| KR | 20080002023 A | 1/2008 |
| KR | 20080080513 A | 9/2008 |
| KR | 20100033265 A | 3/2010 |
| KR | 20110090566 A | 8/2011 |
| KR | 20110111967 A | 10/2011 |
| KR | 20120061503 A | 6/2012 |
| KR | 20120112277 A | 10/2012 |
| KR | 20140132562 A | 11/2014 |
| KR | 20160041124 A | 4/2016 |
| TW | 201332972 A | 8/2013 |
| WO | 2015050253 A1 | 4/2015 |

OTHER PUBLICATIONS

Machine translated English version, WO 2012/005360, Masui Kensuke, Jan. 12, 2012 (Year: 2012).*
Richard D. Hreha et al. "2,7-Bis(diarylamino) 9,9-dimethylfuorenes as Hole-Transport Materials for Organic Light-Emitting Diodes" Adv. Func. Mater. 2003, vol. 13, p. 967-973 (Year: 2003).*
Yuan-Li Liao et al. "Hole Mobilities of 2,7- and 2,2'-Disubstituted 9,9'-Spirobifluorene-Based Triaryldiamines and Their Application as Hole Transport Materials in OLEDs" Chem. Mater. 2007, vol. 19, p. 6350-6357 (Year: 2007).*
Kenji Okumoto et al. "New Hole-Transporting Amorphous Molecular Materials with High Glass-Transition Temperatures for Organic Light-Emitting Diodes", Chem. Letts, 2000, vol. p. 1034-1035 (Year: 2000).*
English translation of KR 2014/0142923 A and the original KR 2014/0142923 A, Moonsung Kang, Dec. 15, 2014 (Year: 2014).*
English translation of KR 101565039 and the original KR 101565039, Soon-Chang Lee, Nov. 2, 2015 (Year: 2015).*
English translation of JPH11-054280 and the original JPH11-054280, Manabu Uchida (Year: 1996).*
English translation of JPH11-273860 and the original JPH11-273860, Tamano Michiko (Year: 1996).*
Wei Jiang et al. "A high triplet energy small molecule based thermally cross-linkable hole-transporting material for solution-processed multilayer blue electrophosphorescent devices" J. Mater. Chem. C, 2015, vol. 3, p. 243-246 (Year: 2015).*
International Search Report for PCT/KR2017/001555 mailed May 23, 2017.
Extended European Search Report including the Written Opinion for Application No. EP 17786075.6 dated Apr. 17, 2019.
Lengvinaite, et al: "Cross-Linkable Aromatic Amines as Materials for Insoluble Hole-Transporting Layers in Light-Emitting Devices", Synthetic Metals, Elsevier Sequoia, Lausanne, CH, vol. 158, No. 6, Mar. 4, 2008 (Mar. 4, 2008), pp. 213-218.

* cited by examiner

【FIG. 1】
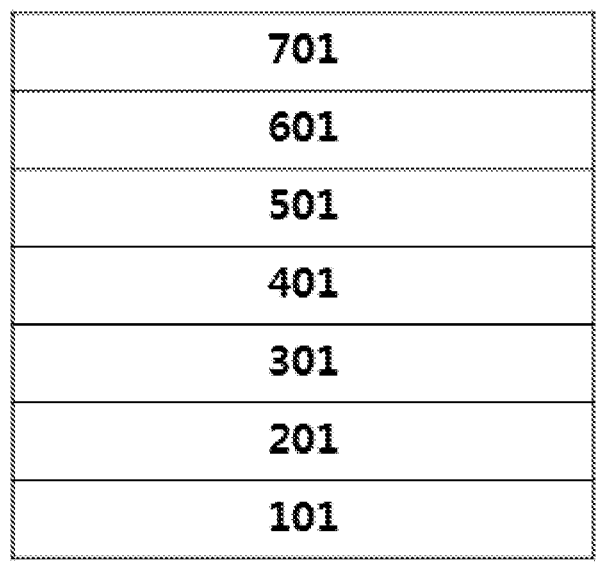
【FIG. 2】
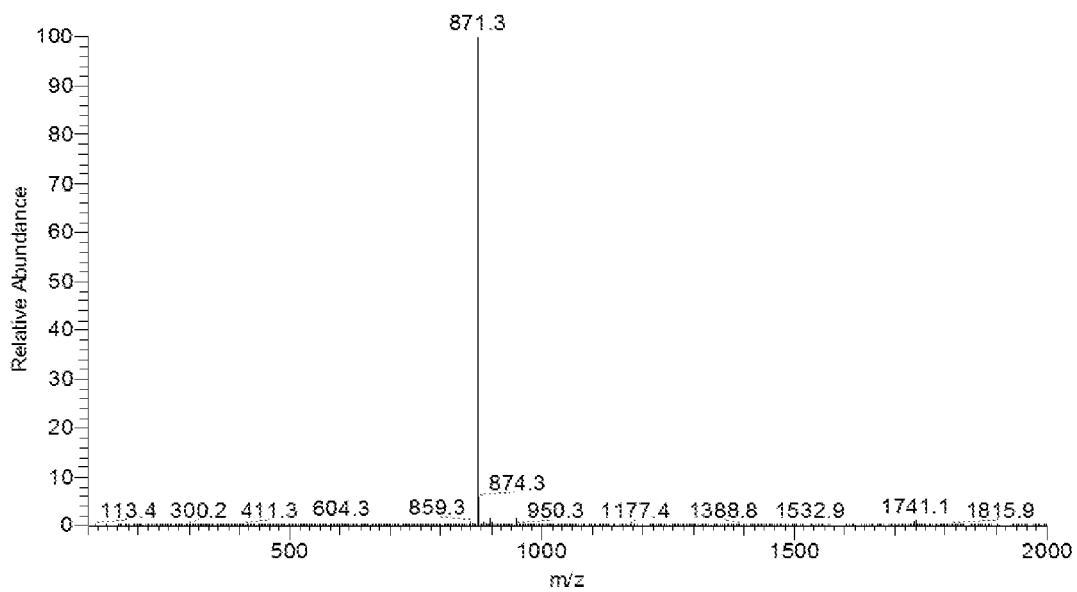

[FIG. 3]
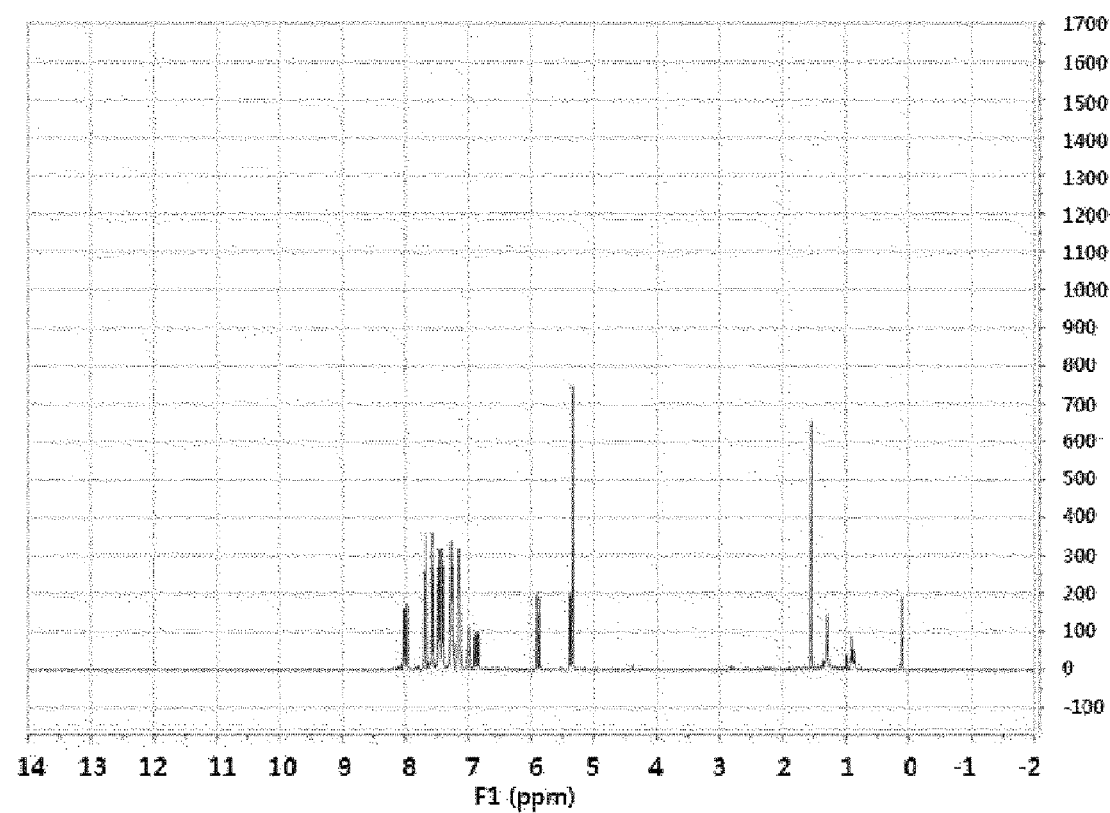

[FIG. 4]
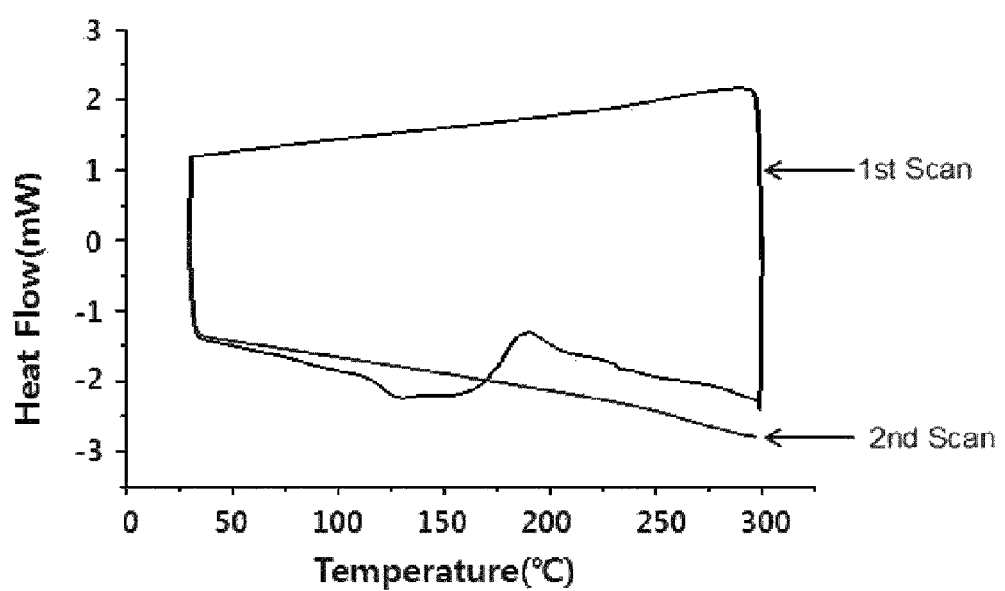

CARBAZOLE DERIVATIVE AND ORGANIC LIGHT EMITTING ELEMENT USING SAME

CROSS-REFERENCE TO RELATED APPLICATIONS

This application is a national phase entry under 35 U.S.C. § 371 of International Application No. PCT/KR2017/001555, filed Feb. 13, 2017, which claims priority to Korean Patent Application No. 10-2016-0049481, filed Apr. 22, 2016, the disclosures of which are incorporated herein by reference.

TECHNICAL FIELD

The present specification relates to a carbazole derivative, a coating composition including the carbazole derivative, an organic light emitting device formed using the coating composition and a method for manufacturing the same.

BACKGROUND ART

An organic light emission phenomenon is one of examples converting current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle is generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferable that materials used in an organic light emitting device additionally have properties as follows.

First, materials used in an organic light emitting device preferably have excellent thermal stability. This is due to joule heating produced by charge transfer in the organic light emitting device. NPB normally used as a hole transfer layer material currently has a glass transition temperature of 100° C. or lower, and is difficult to be used in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifespan.

In addition thereto, materials used in an organic light emitting device need to have excellent chemical stability, degree of charge transfer, and interface properties with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials need to improve an interface with electrodes including metals or metal oxides.

Accordingly, development of organic materials satisfying such requirements has been required in the art.

DISCLOSURE

Technical Problem

The present specification is directed to providing a carbazole derivative capable of being used in an organic light emitting device and satisfying conditions described above, and an organic light emitting device including the same.

Technical Solution

One embodiment of the present specification provides a carbazole derivative represented by the following Chemical Formula 1.

A1-B1-(C1)$n1$-(D)$m$-(C2)$n2$-B2-A2          [Chemical Formula 1]

In Chemical Formula 1,
A1 and A2 are the same as or different from each other, and each independently hydrogen; or a substituted or unsubstituted aryl group,
B1 and B2 are the same as or different from each other, and each independently represented by the following Chemical Formula 2,
C1 and C2 are the same as or different from each other and each independently -L1-NR'-L2-, and L1 and L2 are the same as or different from each other and each independently a direct bond; or substituted or unsubstituted arylene, R' is a substituted or unsubstituted aryl group; or a substituted or unsubstituted heterocyclic group, n1 and n2 are the same as or different from each other and are each an integer of 0 to 2, and when n1 is 2, C1s are the same as or different from each other and when n2 is 2, C2s are the same as or different from each other, D is substituted or unsubstituted arylene, m is an integer of 0 to 2, and when m is 2, Ds are the same as or different from each other,

[Chemical Formula 2]

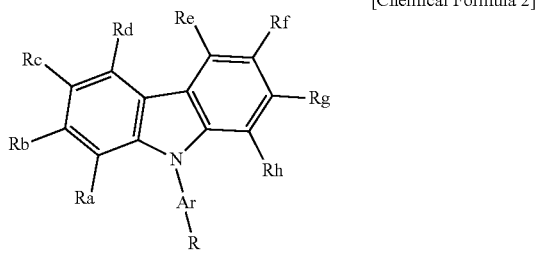

in Chemical Formula 2, one of Ra to Rh bonds to A1 or A2 and another of Ra to Rh bonds to C1 or C2, and groups of Ra to Rh not bonding to A1, A2, C1 or C2 are hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group, Ar is a substituted or unsubstituted arylene group, and R is a thermocurable group or a photocurable group.

Another embodiment of the present specification provides a coating composition including the carbazole derivative.

Still another embodiment of the present specification provides an organic light emitting device including a cathode; an anode; and one or more organic material layers provided between the cathode and the anode, wherein one or more layers of the organic material layers are formed using the coating composition.

Yet another embodiment of the present specification provides a method for manufacturing an organic light emitting device including preparing a substrate; forming a cathode or an anode on the substrate; forming one or more organic material layers on the cathode or the anode; and forming an anode or a cathode on the organic material layers, wherein the forming of organic material layers includes forming one or more organic material layers using the coating composition.

Advantageous Effects

A carbazole derivative according to one embodiment of the present specification is capable of a solution process, and large area devices can be obtained. A carbazole derivative according to one embodiment of the present specification can be used as a material of an organic material layer of an organic light emitting device, and can provide a low driving voltage, high light emission efficiency and a high lifespan property. An organic material layer formed using a carbazole derivative according to one embodiment of the present specification has excellent thermal stability.

DESCRIPTION OF DRAWINGS

FIG. 1 illustrates an organic light emitting device according to one embodiment of the present specification.

FIG. 2 is a diagram showing an MS spectrum of Chemical Formula 1-1-1.

FIG. 3 is a diagram showing a 1H NMR spectrum of Chemical Formula 1-1-1.

FIG. 4 is a diagram showing a differential scanning calorimetry (DSC) of Chemical Formula 1-1-1.

REFERENCE NUMERAL

101: Substrate
201: Anode
301: Hole Injection Layer
401: Hole Transfer Layer
501: Light Emitting Layer
601: Electron Transfer Layer
701: Cathode

MODE FOR DISCLOSURE

Hereinafter, the present specification will be described in detail.

In the present specification, a description of a certain member being placed "on" another member includes not only a case of the certain member adjoining the another member but a case of still another member being present between the two members.

In the present specification, a description of a certain part "including" certain constituents means capable of further including other constituents, and does not exclude other constituents unless particularly stated on the contrary.

In the whole present specification, the term "combination thereof" included in the expression of Markush form means a mixture or a combination of one or more selected from the group consisting of constituents described in the expression of Markush form, and means including one or more selected from the group consisting of the constituents.

One embodiment of the present specification provides a carbazole derivative represented by Chemical Formula 1. Factors affecting a curing temperature lowers the curing temperature as the curing group is further away from the compound center rather than locating in the compound center. Particularly, in the structure of Chemical Formula 1, the location of a thermocurable group or a photocurable group is away from the compound center even when the molecular weight increases with an increase in the length of linker D. Accordingly, a thermocuring temperature advantageous for a process may be obtained by a thermocurable group or a photocurable group locating on a 9-position of the carbazole group in the structure of Chemical Formula 1.

According to one embodiment of the present specification, compounds going through curing in a thermocuring temperature range of 300° C. or lower are preferred among the compounds of Chemical Formula 1, and compounds having solubility for proper organic solvents are preferred.

In the present specification, "thermocurable group or photocurable group" means a reactive substituent crosslinking compounds by being exposed to heat and/or light. The crosslinkage may be produced while radicals produced as carbon-carbon multiple bonds and cyclic structures are decomposed by heat treatment or light irradiation are linked.

For example, a thermocurable group or a photocurable group is

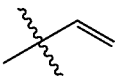 [SMILES: *C=C]

and the thermocurable group or the photocurable group may be linked to other carbazole derivatives with a structure of

crosslinked by heat treatment or light treatment.

In one embodiment of the present specification, the thermocurable group or the photocurable group is any one of the following structures.

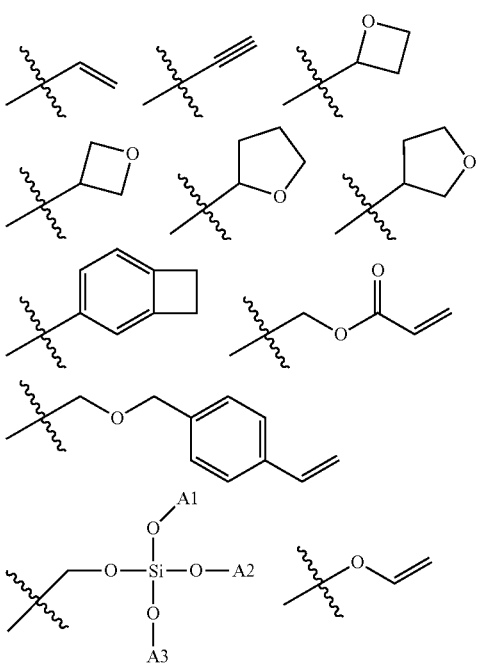

In the structures, A1 to A3 are the same as or different from each other, and each independently a substituted or unsubstituted alkyl group having 1 to 6 carbon atoms.

As in one embodiment of the present specification, an organic light emitting device may be manufactured using a solution coating method with a carbazole derivative including a thermocurable group or a photocurable group, which is economically effective in terms of time and costs.

In addition, when forming a coating layer using a coating composition including a carbazole derivative including a thermocurable group or a photocurable group, the thermocurable group or the photocurable group forms crosslinkage by heat or light, and therefore, the carbazole derivative included in the coating composition being washed away by a solvent is prevented when laminating additional layers on the top of the coating layer, and additional layers may be laminated on the top of the coating layer while retaining the coating layer.

Additionally, when the coating layer is formed by a thermocurable group or a photocurable group forming crosslinkage, effects of increasing chemical resistance of the coating layer for a solvent and having a high film retention rate are obtained.

In addition, in the carbazole derivative according to one embodiment of the present specification, an organic light emitting device may be manufactured using a solution coating method, which enables manufacture of large-area devices.

According to one embodiment of the present specification, in the carbazole derivative in which crosslinkage is formed by heat treatment or light irradiation, a plurality of carbazole derivatives are crosslinked and provided in an organic light emitting device in a thin film form, and therefore, an effect of having excellent thermal stability is obtained. Accordingly, an organic light emitting device using the carbazole derivative according to one embodiment of the present specification is effective in obtaining an excellent lifespan property.

In addition, the carbazole derivative according to one embodiment of the present specification includes an amine structure in the core structure, and therefore, is capable of having proper energy level and band gap as a hole injection material, a hole transfer material or a light emitting material in an organic light emitting device. In addition, by controlling substituents of the compound of Chemical Formula 1 according to one embodiment of the present specification, proper energy level and band gap may be minutely controlled, and by enhancing an interfacial property between organic materials, an organic light emitting device having a low driving voltage and high light emission efficiency may be provided.

Hereinafter, substituents of the present specification will be described in detail.

In the present specification,

means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of hydrogen; deuterium; a halogen group; a nitrile group; a nitro group; a hydroxyl group; an alkyl group; an alkoxy group; an alkenyl group; an aryl group; an amine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, examples of the halogen group may include fluorine, chlorine, bromine or iodine.

In the present specification, the alkyl group may be linear, branched or cyclic, and the number of carbon atoms is not particularly limited, but is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

The alkyl group may be substituted with an aryl group or a heteroaryl group to function as an arylalkyl group or a heteroarylalkyl group. The aryl group or the heterocyclic group may be selected from among examples of the aryl group or the heterocyclic group to be described below.

In the present specification, the length of the alkyl group does not affect a conjugation length of a compound, and may affect a method of using the compound in an organic light emitting device, for example, use of a vacuum deposition method or a solution coating method.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkoxy group may be substituted with an aryl group or a heteroaryl group to function as an aryloxy group or a heteroaryloxy group. The aryl group or the heterocyclic group may be selected from among examples of the aryl group or the heterocyclic group to be described below.

In the present specification, the alkenyl group may be linear or branched, and although not particularly limited thereto, the number of carbon atoms is preferably from 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

The alkenyl group may be substituted with an aryl group or a heteroaryl group to function as an arylalkenyl group or a heteroarylalkenyl group. The aryl group or the heterocyclic group may be selected from among examples of the aryl group or the heterocyclic group to be described below.

When the aryl group is a monocyclic aryl group in the present specification, the number of carbon atoms is not particularly limited, but is preferably from 6 to 25. Specific examples of the monocyclic aryl group may include a phenyl group, a biphenyl group, a terphenyl group, a quaterphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

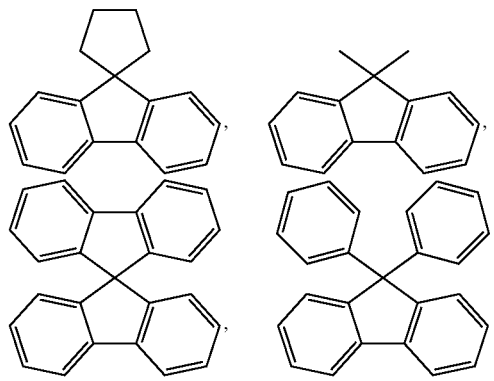

and the like may be included. However, the compound is not limited thereto.

The aryl group may be substituted with an alkyl group to function as an arylalkyl group. The alkyl group may be selected from among the examples described above.

In the present specification, the heterocyclic group includes one or more atoms that are not carbon, that is, heteroatoms, and specifically, the heteroatom may include one or more atoms selected from the group consisting of O, N, Se, S and the like. The number of carbon atoms of the heterocyclic group is not particularly limited, but is preferably from 2 to 60. Examples of the heterocyclic group may include a thiophene group, a furan group, a pyrrole group, an imidazole group, a thiazole group, an oxazole group, an oxadiazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

The heterocyclic group may be monocyclic or multicyclic, and may be aromatic, aliphatic or a fused ring of aromatic and aliphatic.

In the present specification, the number of carbon atoms of the amine group is not particularly limited, but is preferably from 1 to 30. The amine group may be substituted with the alkyl group, the aryl group, the heterocyclic group, the alkenyl group and the cycloalkyl group described above, and combinations thereof. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, the arylamine group means an amine group substituted with an aryl group, and examples described above may be used on the aryl group.

In the present specification, the arylene group may be selected from among the examples of the aryl group described above, except that the arylene group is divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the ring formed by adjacent groups bonding to each other may be monocyclic or multicyclic, may be aliphatic, aromatic, or a fused ring of aliphatic and aromatic, and may form a hydrocarbon ring or a heteroring.

The hydrocarbon ring may be selected from among the examples of the cycloalkyl group or the aryl group except for those that are not monovalent. The heteroring may be aliphatic, aromatic, or a fused ring of aliphatic and aromatic, and may be selected from among the examples of the heterocyclic group except for those that are not monovalent.

In one embodiment of the present specification, L1 and L2 are the same as or different from each other and a direct bond or phenylene, and R' is a phenyl group unsubstituted or substituted with at least one of a substituted or unsubstituted aryl group, a substituted or unsubstituted heterocyclic group, a substituted or unsubstituted alkoxy group, and a substituted or unsubstituted arylamine group.

In one embodiment of the present specification, L1 and L2 are the same as or different from each other and a direct bond or phenylene, and R' is a phenyl group unsubstituted or substituted with at least one of an aryl group, a heterocyclic group, an alkoxy group and an arylamine group.

In one embodiment of the present specification, L1 and L2 are the same as or different from each other and a direct bond or phenylene, and R' is a phenyl group unsubstituted or substituted with at least one of an aryl group and an arylamine group.

In one embodiment of the present specification, C1 and C2 are the same as or different from each other, and each independently represented by the following structural formulae.

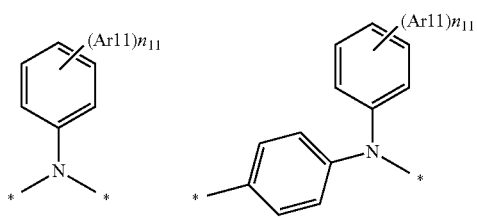

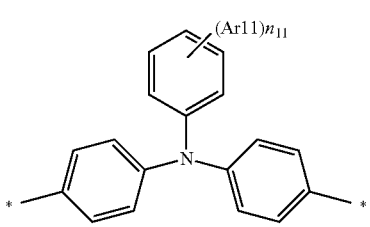

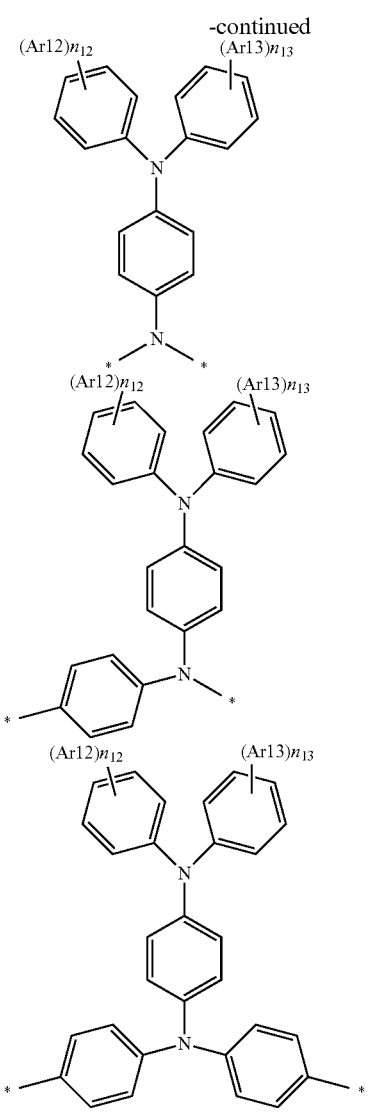

In the structural formulae, Ar11 to Ar13 are the same as or different from each other and each independently hydrogen; a substituted or unsubstituted aryl group; a substituted or unsubstituted alkoxy group; a substituted or unsubstituted arylamine group; or a substituted or unsubstituted heterocyclic group, and n11 to n13 are the same as or different from each other and are each an integer of 0 to 5, and when these are 2 or greater, structures in the parentheses are the same as or different from each other.

According to one embodiment, Ar11 to Ar13 are the same as or different from each other, and each independently hydrogen; an aryl group; an alkoxy group; an arylamine group; or a heterocyclic group.

According to one embodiment, Ar11 to Ar13 are the same as or different from each other, and each independently hydrogen; an aryl group; or an arylamine group.

According to one embodiment, Ar11 to Ar13 are the same as or different from each other, and each independently hydrogen; a phenyl group; a biphenylyl group; a diphenylamine group; or a dibiphenylylamine group.

According to another embodiment, Chemical Formula 1 is represented by the following Chemical Formula 3:

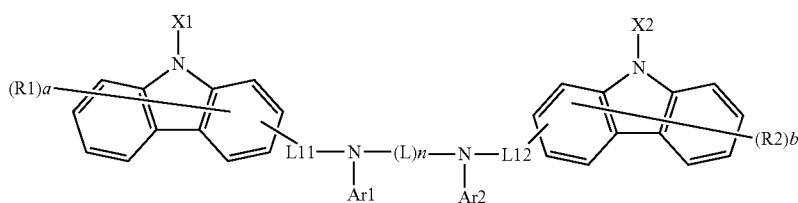

[Chemical Formula 3]

In Chemical Formula 3,

X1 and X2 are the same as or different from each other, and each independently an aryl group substituted with a thermocurable group or a photocurable group, a and b are each an integer of 1 to 7, when a and b are each 2 or greater, structures in the parentheses are the same as or different from each other, R1 and R2 are the same as or different from each other, and each independently hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group, Ar1 and Ar2 are the same as or different from each other, and each independently a substituted or unsubstituted aryl group; or a substituted or unsubstituted heterocyclic group, L is a substituted or unsubstituted arylene group, L11 and L12 are the same as or different from each other, and each independently a direct bond; or a substituted or unsubstituted arylene group, n is 1 or 2, and when n is 2, Ls are the same as or different from each other.

According to another embodiment, Chemical Formula 1 is represented by the following Chemical Formula 4:

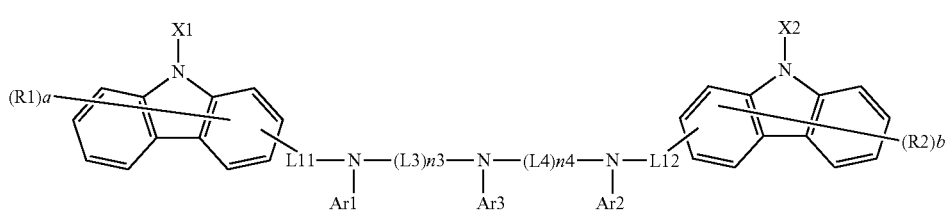

[Chemical Formula 4]

In Chemical Formula 4,

X1 and X2 are the same as or different from each other, and each independently an aryl group substituted with a thermocurable group or a photocurable group, a and b are each an integer of 1 to 7, when a and b are each 2 or greater, structures in the parentheses are the same as or different from each other, R1 and R2 are the same as or different from each other, and each independently hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group, Ar1 to Ar3 are the same as or different from each other, and each independently a substituted or unsubstituted aryl group; or a substituted or unsubstituted heterocyclic group, L3 and L4 are the same as or different from each other and each independently a substituted or unsubstituted arylene group, n3 and n4 are 1 or 2, and when n3 is 2, L3s are the same as or different from each other and when n4 is 2, L4s are the same as or different from each other, and L11 and L12 are the same as or different from each other, and each independently a direct bond; or a substituted or unsubstituted arylene group.

According to another embodiment, Chemical Formula 1 is represented by the following Chemical Formula 5:

[Chemical Formula 5]

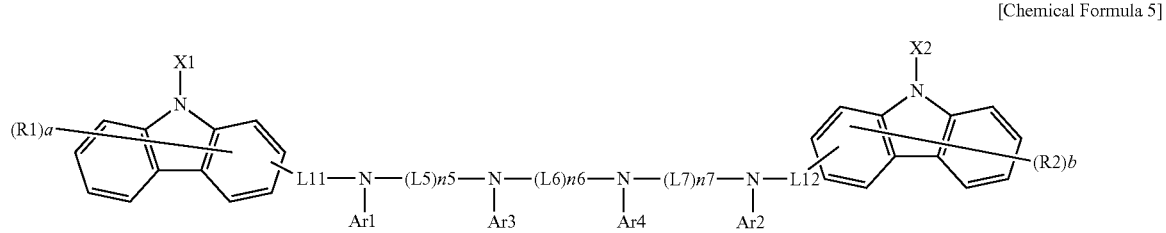

In Chemical Formula 5,

X1 and X2 are the same as or different from each other, and each independently an aryl group substituted with a thermocurable group or a photocurable group, a and b are each an integer of 1 to 7, when a and b are each 2 or greater, structures in the parentheses are the same as or different from each other, R1 and R2 are the same as or different from each other, and each independently hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group, Ar1 to Ar4 are the same as or different from each other, and each independently a substituted or unsubstituted aryl group; or a substituted or unsubstituted heterocyclic group, L5 to L7 are the same as or different from each other and each independently a substituted or unsubstituted arylene group, n5 to n7 are 1 or 2, and when n5 is 2, L5s are the same as or different from each other, when n6 is 2, L6s are the same as or different from each other and when n7 is 2, L7s are the same as or different from each other, and L11 and L12 are the same as or different from each other, and each independently a direct bond; or a substituted or unsubstituted arylene group.

According to another embodiment, Chemical Formula 1 is represented by one of the following Chemical Formulae 6 to 9:

[Chemical Formula 6]

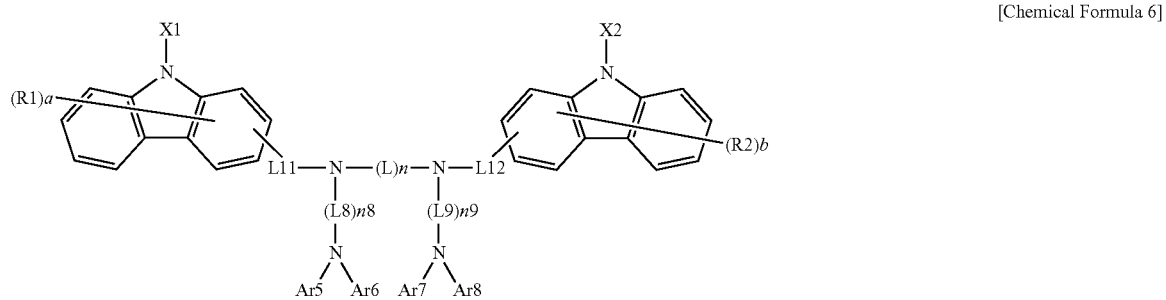

[Chemical Formula 7]

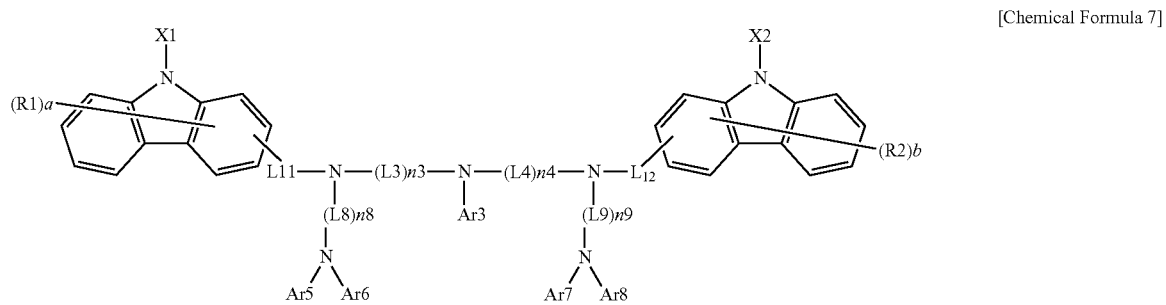

-continued

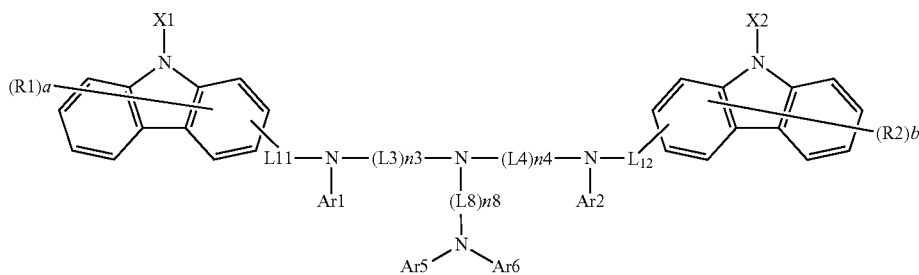
[Chemical Formula 8]

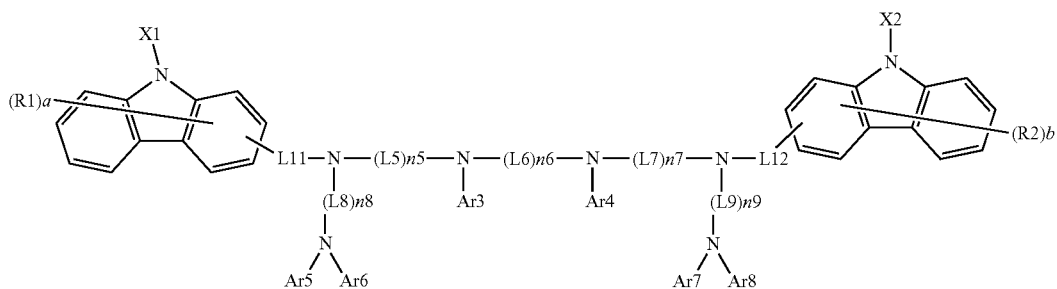
[Chemical Formula 9]

In Chemical Formulae 6 to 9,

X1 and X2 are the same as or different from each other, and each independently an aryl group substituted with a thermocurable group or a photocurable group, a and b are each an integer of 1 to 7, when a and b are each 2 or greater, structures in the parentheses are the same as or different from each other, R1 and R2 are the same as or different from each other, and each independently hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group, Ar1 to Ar8 are the same as or different from each other, and each independently a substituted or unsubstituted aryl group; or a substituted or unsubstituted heterocyclic group, L and L3 to L9 are the same as or different from each other and each independently a substituted or unsubstituted arylene group, n and n3 to n9 are 1 or 2, and when n is 2, Ls are the same as or different from each other, when n3 is 2, L3s are the same as or different from each other, when n4 is 2, L4s are the same as or different from each other, when n5 is 2, L5s are the same as or different from each other, when n6 is 2, L6s are the same as or different from each other, when n7 is 2, L7s are the same as or different from each other, when n8 is 2, L6s are the same as or different from each other and when n9 is 2, L9s are the same as or different from each other, and L11 and L12 are the same as or different from each other, and each independently a direct bond; or a substituted or unsubstituted arylene group.

According to another embodiment, Chemical Formula 1 is represented by one of the following Chemical Formulae 10 to 12:

[Chemical Formula 10]

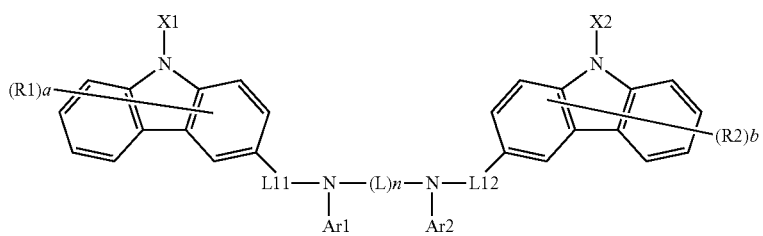

[Chemical Formula 11]

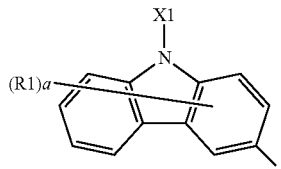 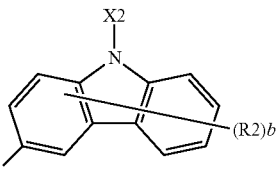

[Chemical Formula 12]

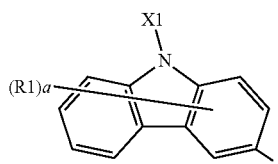 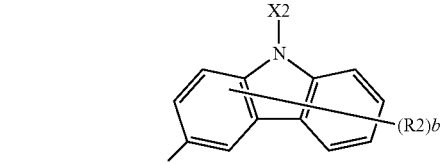

In Chemical Formulae 10 to 12,

X1 and X2 are the same as or different from each other, and each independently an aryl group substituted with a thermocurable group or a photocurable group, a and b are each an integer of 1 to 7, when a and b are each 2 or greater, structures in the parentheses are the same as or different from each other, R1 and R2 are the same as or different from each other, and each independently hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group, Ar1 to Ar4 are the same as or different from each other, and each independently a substituted or unsubstituted aryl group; or a substituted or unsubstituted heterocyclic group, L and L3 to L7 are the same as or different from each other and each independently a substituted or unsubstituted arylene group, n and n3 to n7 are 1 or 2, and when n is 2, Ls are the same as or different from each other, when n3 is 2, L3s are the same as or different from each other, when n4 is 2, L4s are the same as or different from each other, when n5 is 2, L5s are the same as or different from each other, when n6 is 2, L6s are the same as or different from each other and when n7 is 2, L7s are the same as or different from each other, and L11 and L12 are the same as or different from each other, and each independently a direct bond; or a substituted or unsubstituted arylene group.

According to another embodiment, Chemical Formula 1 is represented by the following Chemical Formula 13:

[Chemical Formula 13]

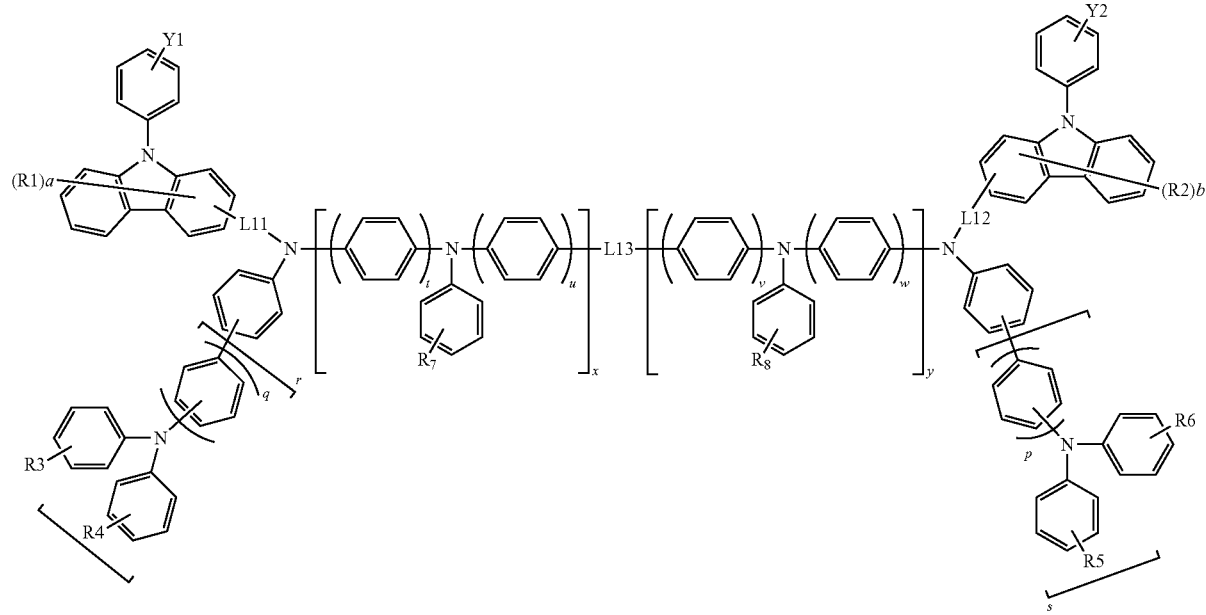

In Chemical Formula 13,
Y1 and Y2 are the same as or different from each other, and each independently a thermocurable group or a photocurable group,
a and b are each an integer of 1 to 7,
when a and b are each 2 or greater, structures in the parentheses are the same as or different from each other,
R1 and R2 are the same as or different from each other, and each independently hydrogen; deuterium; a substituted or unsubstituted alkyl group; a substituted or unsubstituted alkenyl group; a substituted or unsubstituted alkoxy group; a substituted or unsubstituted arylamine group; a substituted or unsubstituted aryl group; or a substituted or unsubstituted heterocyclic group, or adjacent substituents bond to each other to form a substituted or unsubstituted hydrocarbon ring; or a substituted or unsubstituted heterocyclic group,
R3 to R8 are the same as or different from each other, and each independently a substituted or unsubstituted aryl group, a substituted or unsubstituted heterocyclic group, a substituted or unsubstituted alkoxy group, or a substituted or unsubstituted arylamine group, and
L11, L12 and L13 are the same as or different from each other and each independently a direct bond; or a substituted or unsubstituted arylene group, and p, q, r, s, t, u, v, w, x and y are each an integer of 0 to 2.

According to another embodiment, X1 and X2 are the same as or different from each other, and each independently an aryl group having 6 to 30 carbon atoms substituted with a thermocurable group or a photocurable group.

According to another embodiment, X1 and X2 are the same as or different from each other, and each independently a phenyl group substituted with a thermocurable group or a photocurable group.

According to another embodiment, L and L1 to L12 are the same as or different from each other, and each independently arylene unsubstituted or substituted with an alkyl group or an aryl group.

According to another embodiment, L and L1 to L12 are the same as or different from each other, and each independently phenylene, biphenylylene, naphthylene, fluorenylene unsubstituted or substituted with an alkyl group or an aryl group, spirobifluorenylene or phenanthrenylene.

According to another embodiment, L1 to L12 are the same as or different from each other, and each independently phenylene or biphenylylene.

According to another embodiment, L11 and L12 are a direct bond or arylene.

According to another embodiment, L11 and L12 are a direct bond, phenylene or biphenylylene.

According to another embodiment, L11 and L12 are a direct bond or phenylene.

According to another embodiment, Ar1 to Ar8 are the same as or different from each other, and each independently a phenyl group unsubstituted or substituted with at least one of a substituted or unsubstituted aryl group, a substituted or unsubstituted heterocyclic group, a substituted or unsubstituted alkoxy group, and a substituted or unsubstituted arylamine group.

According to another embodiment, Ar1 to Ar8 are the same as or different from each other, and each independently a phenyl group unsubstituted or substituted with at least one of a substituted or unsubstituted aryl group, a substituted or unsubstituted heterocyclic group, a substituted or unsubstituted alkoxy group, and a substituted or unsubstituted arylamine group.

According to another embodiment, R1 to R8 are hydrogen; deuterium; an aryl group; or a heterocyclic group.

According to another embodiment, R1 and R2 are the same as or different from each other, and each independently hydrogen; deuterium; an aryl group; or a heterocyclic group.

According to another embodiment, R1 and R2 are the same as or different from each other, and each independently hydrogen; deuterium; a phenyl group; or a dibenzofuran group.

According to another embodiment, R3 to R8 are hydrogen.

According to another embodiment, D and L13 are an arylene group unsubstituted or substituted with an alkyl group or an aryl group.

According to another embodiment, D and L13 are a monocyclic to hexacyclic arylene group unsubstituted or substituted with an alkyl group or an aryl group.

According to another embodiment, D and L13 are a phenylene group, a biphenylene group, a fluorenylene group unsubstituted or substituted with an alkyl group or an aryl group, a spirobifluorenylene group, a naphthylene group, a phenanthrenylene group, spiro(fluorene-9,8'-indoloacridine), or spiro(acridine-9,9'-fluorene) unsubstituted or substituted with an alkylaryl group or an aryl group.

According to another embodiment, the compound of Chemical Formula 1 may be represented by the following structural formulae.

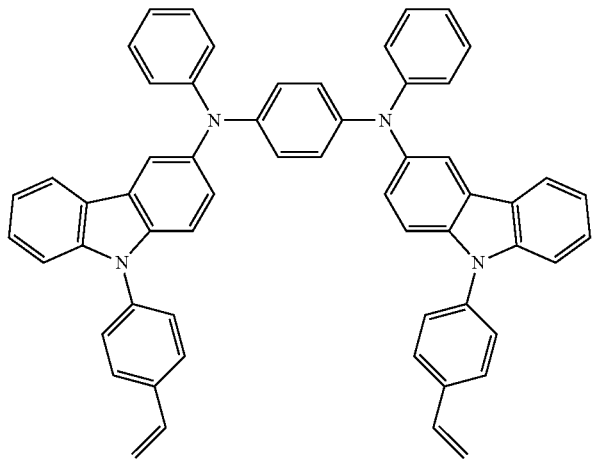

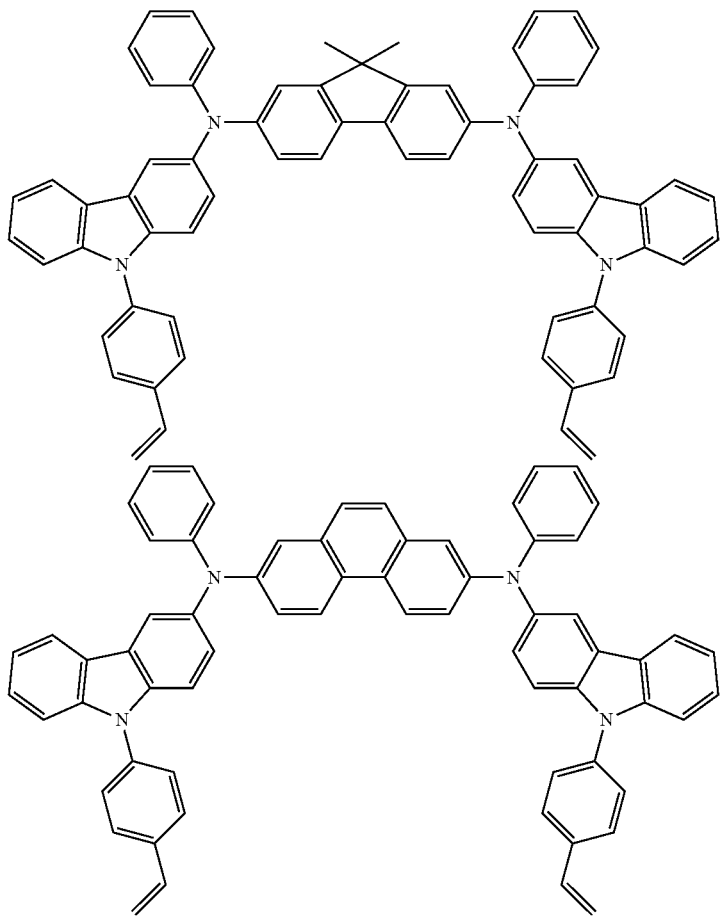

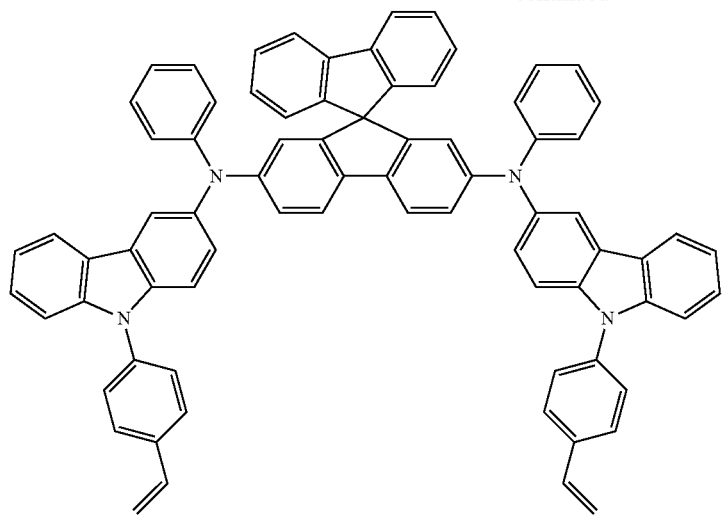
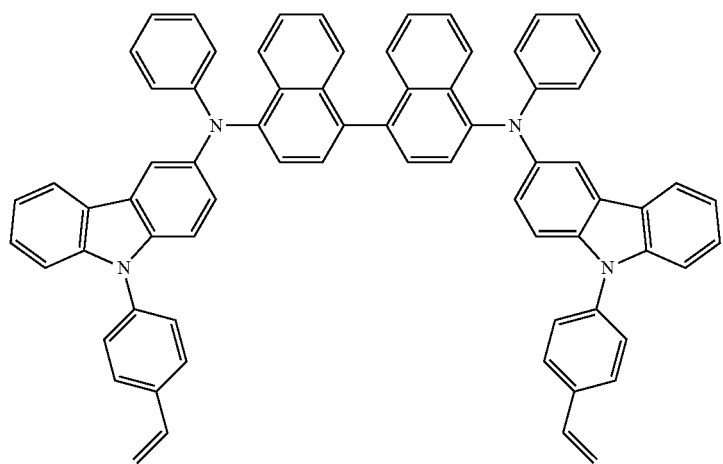
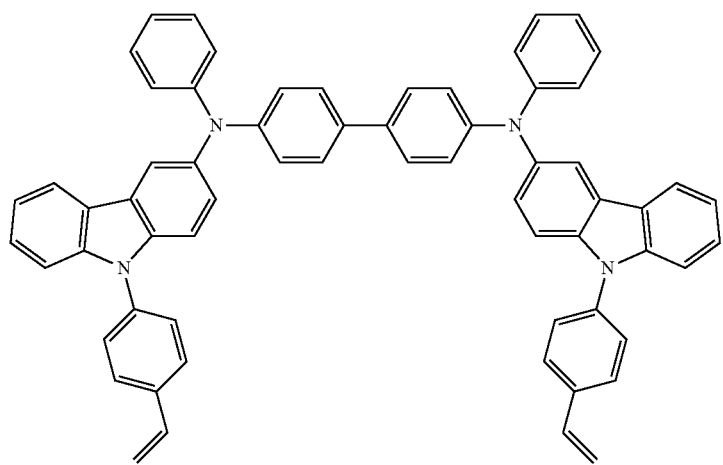

-continued
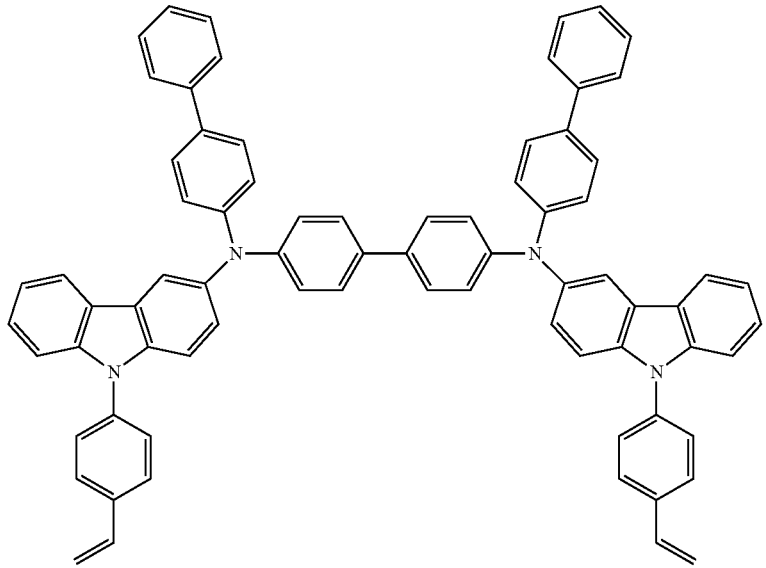
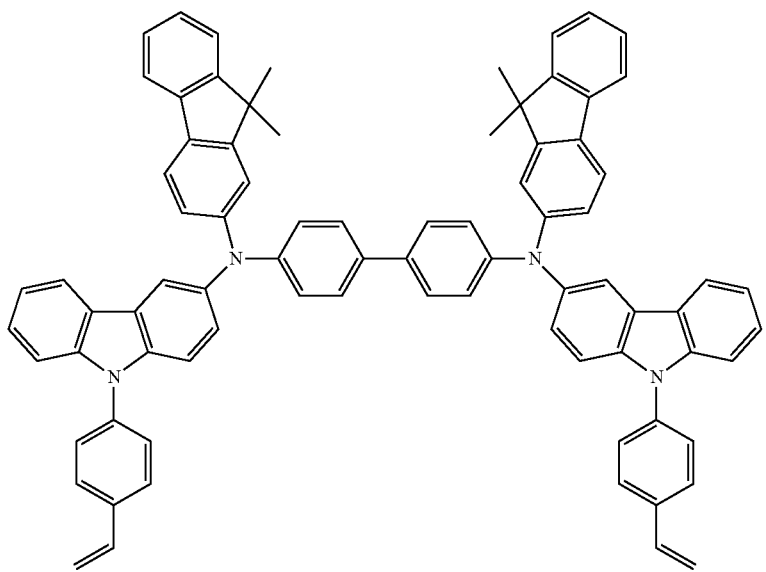
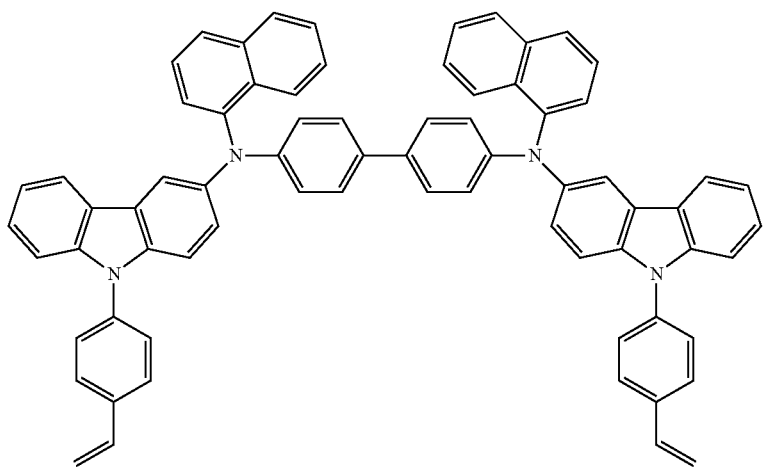

-continued
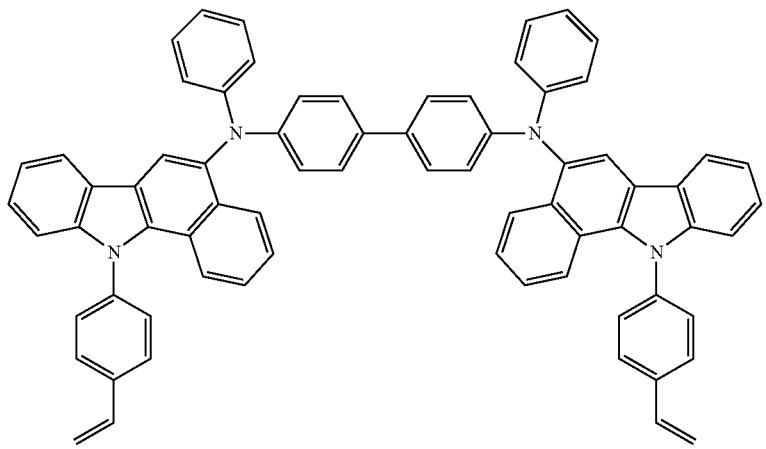
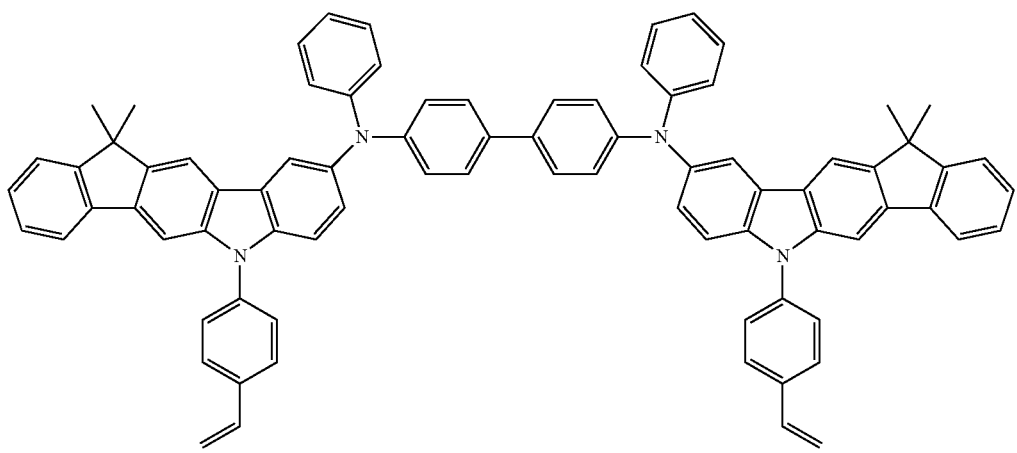
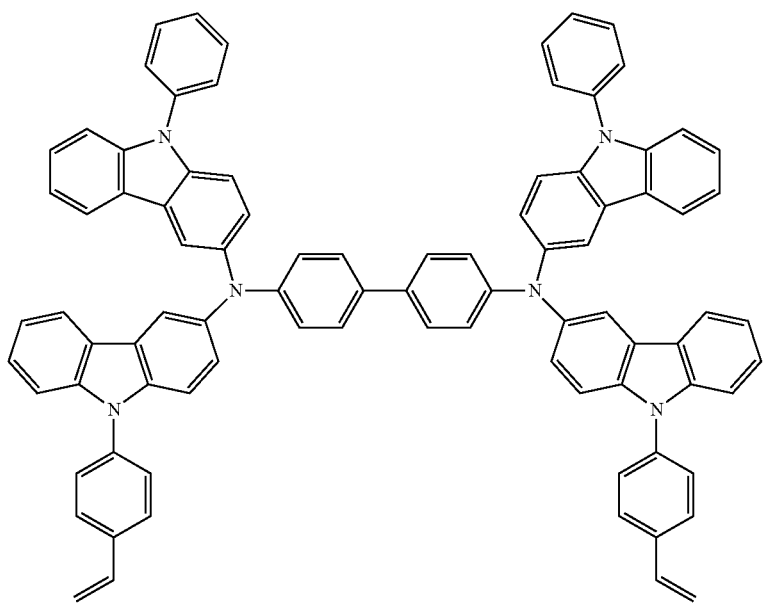

-continued
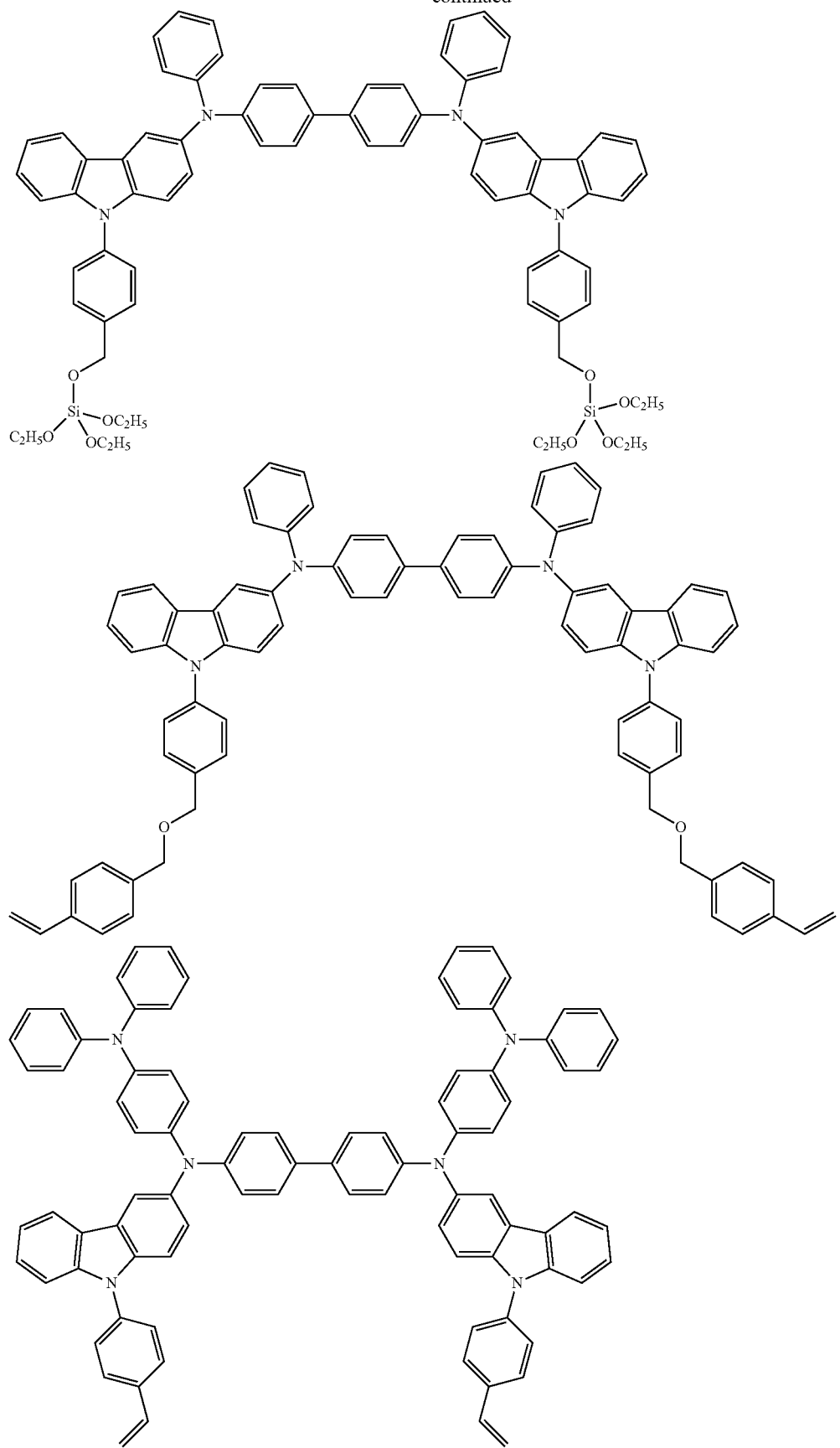

-continued
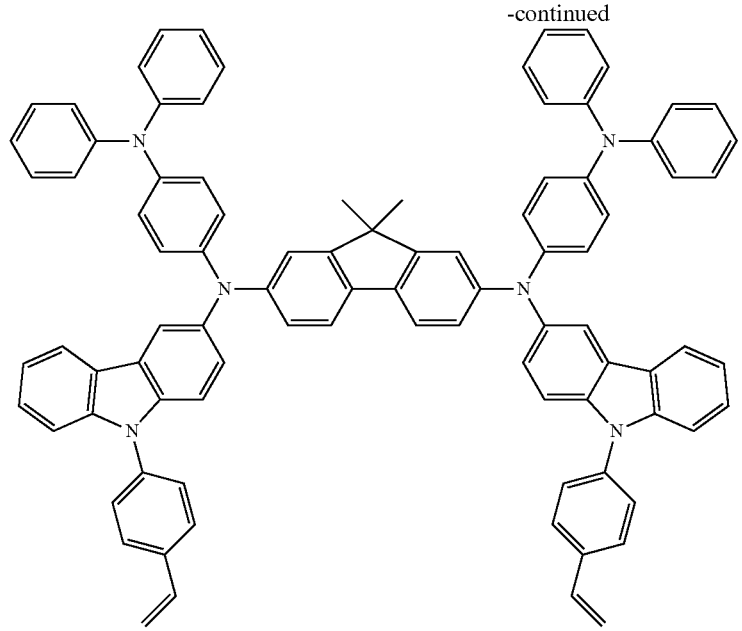
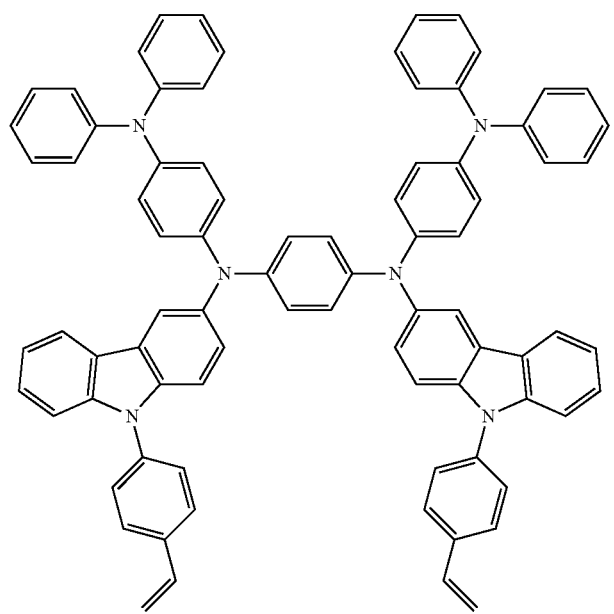

-continued
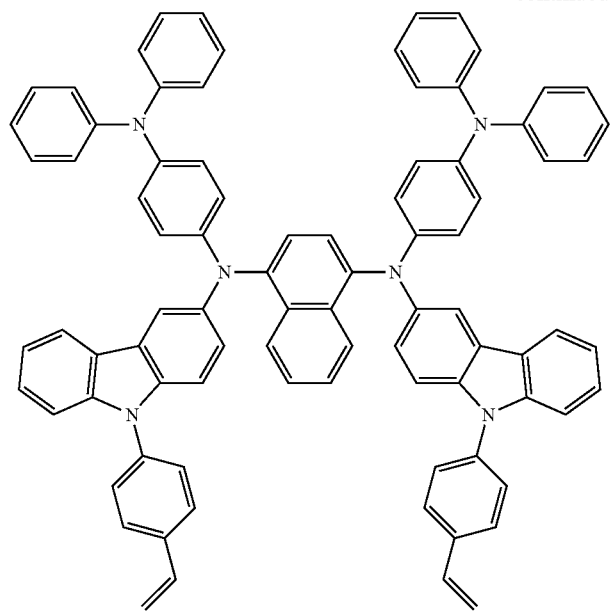
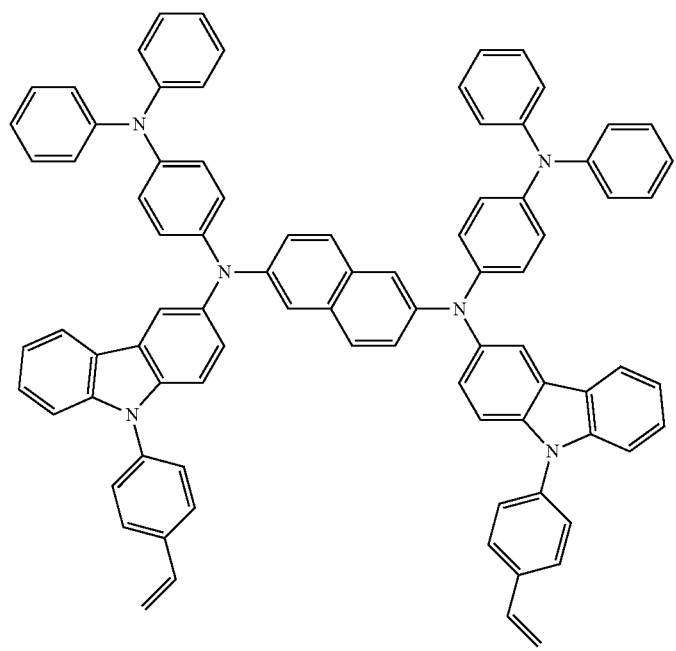
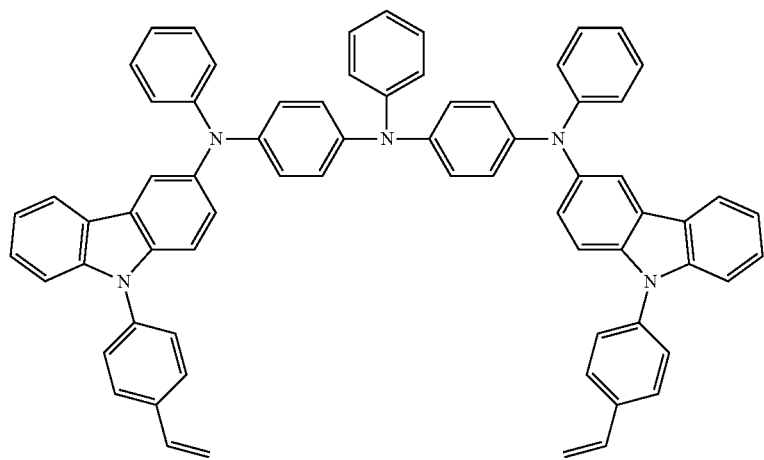

-continued
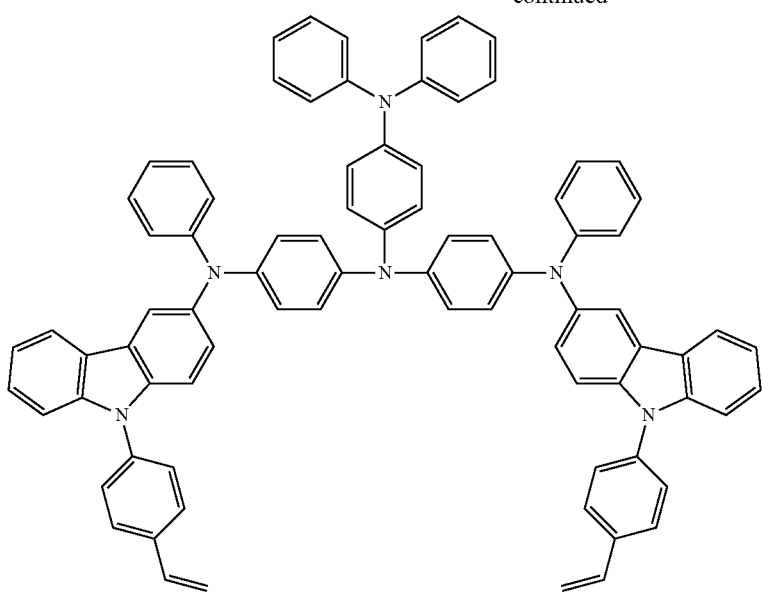
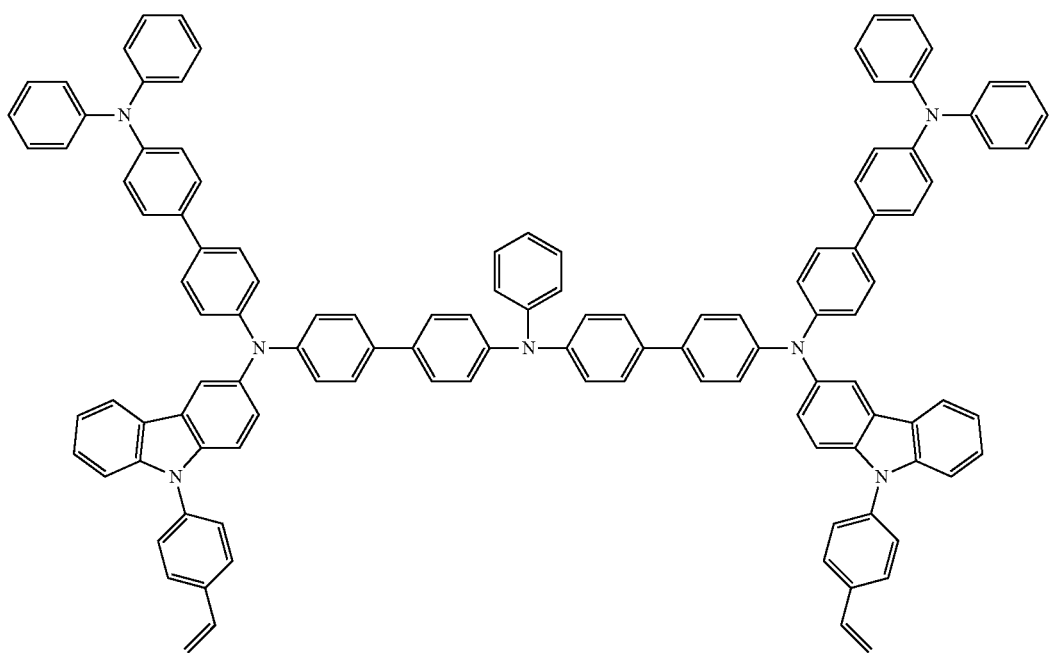

-continued
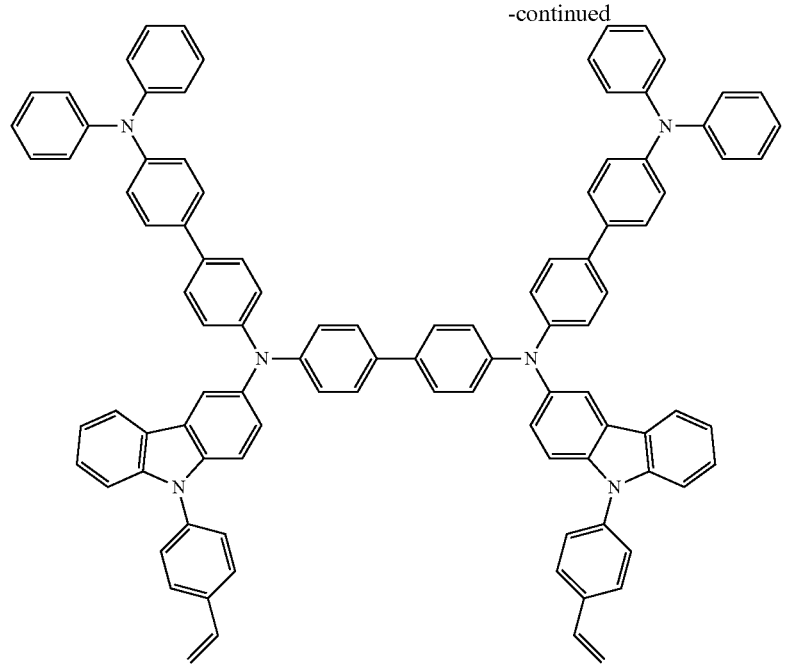
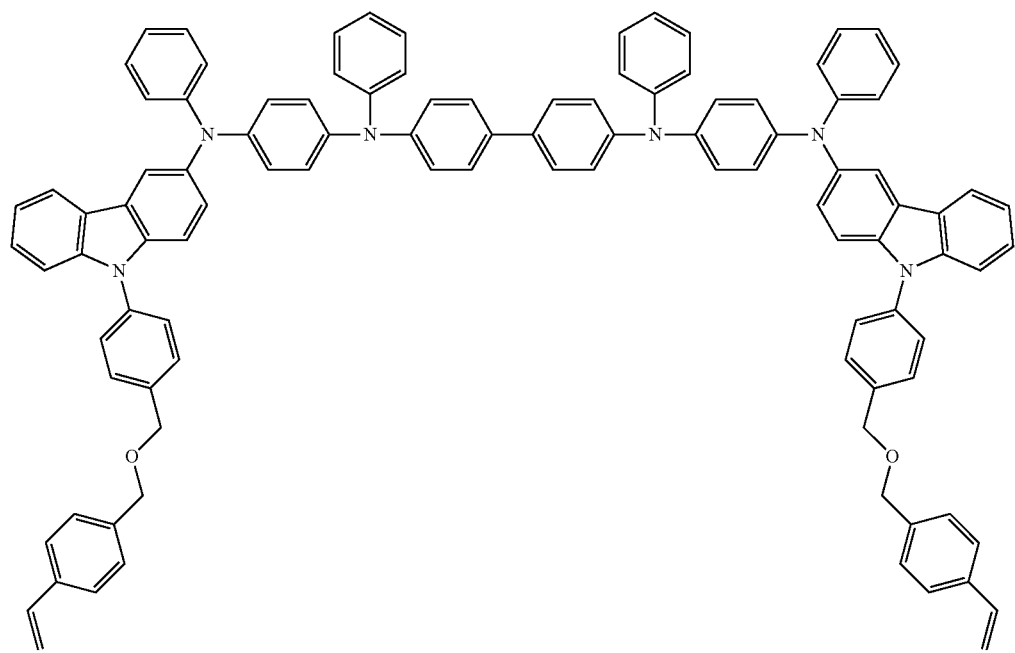

-continued
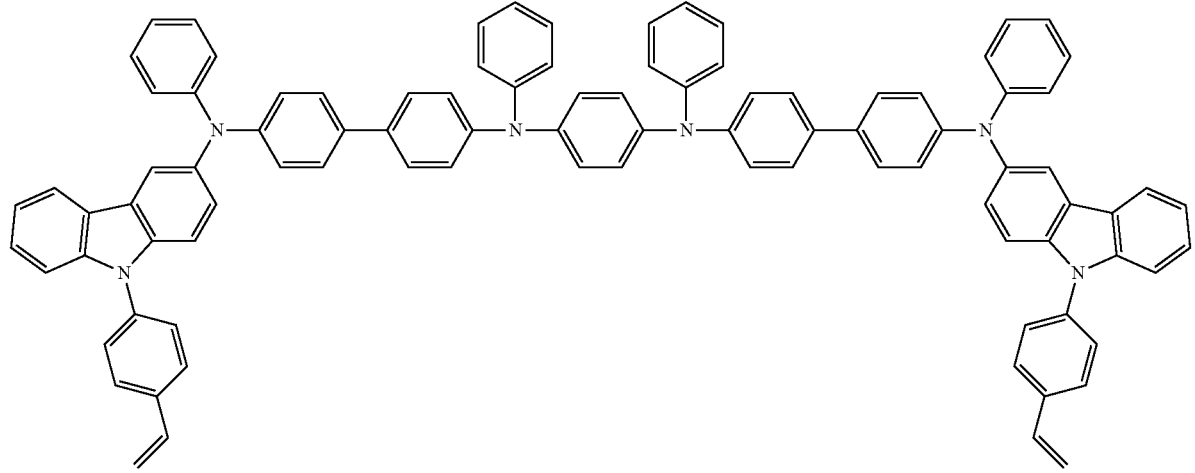
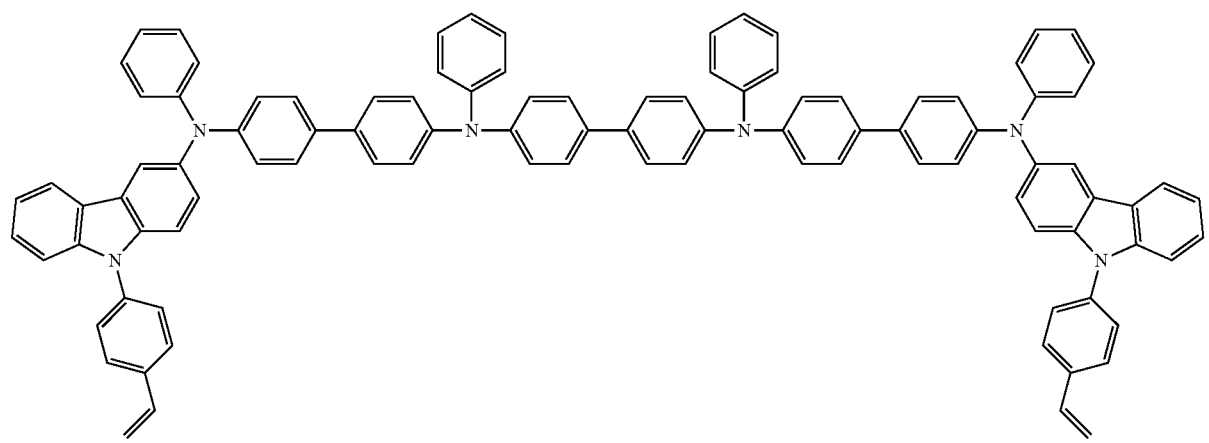
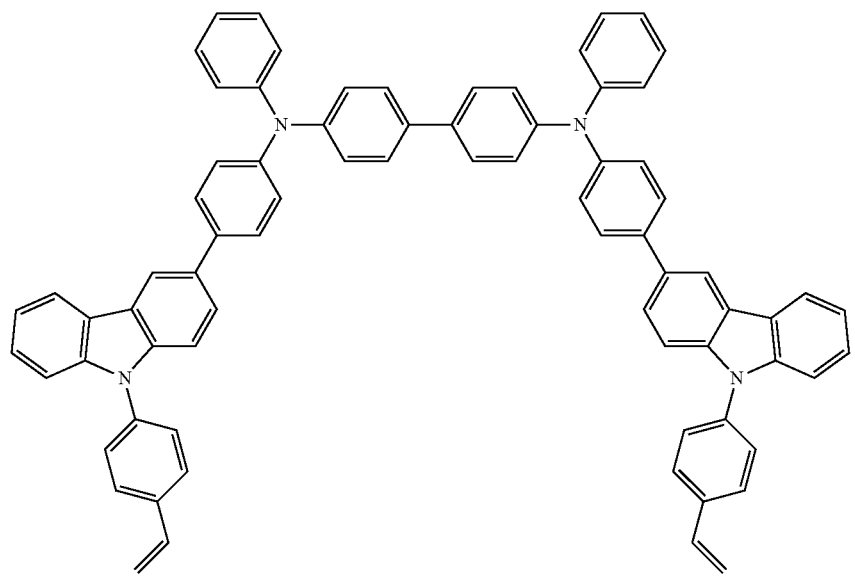

-continued
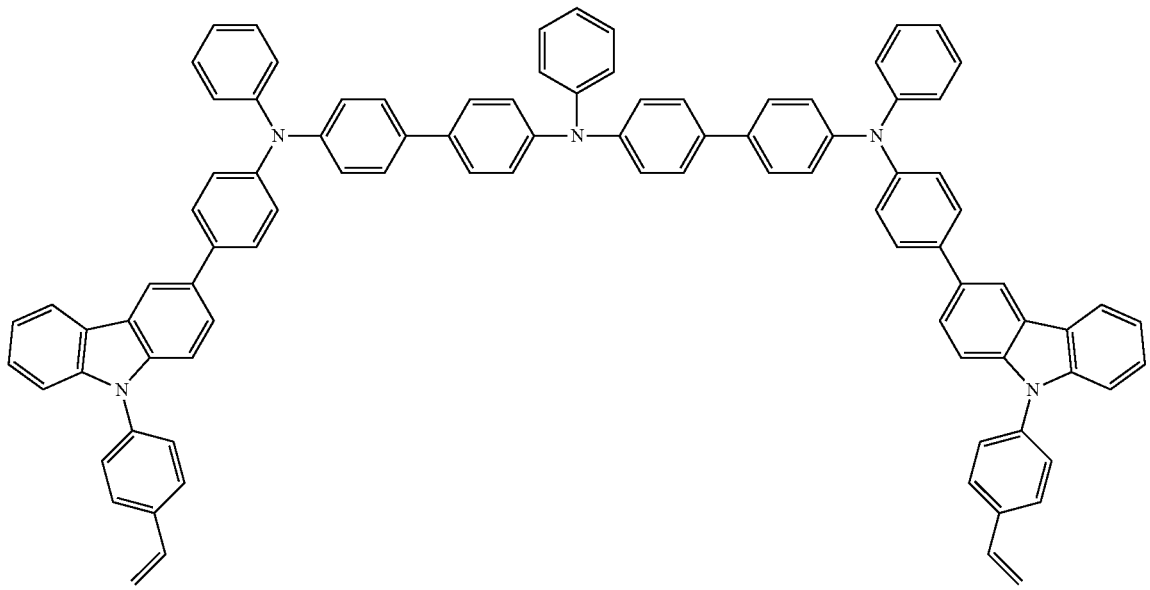
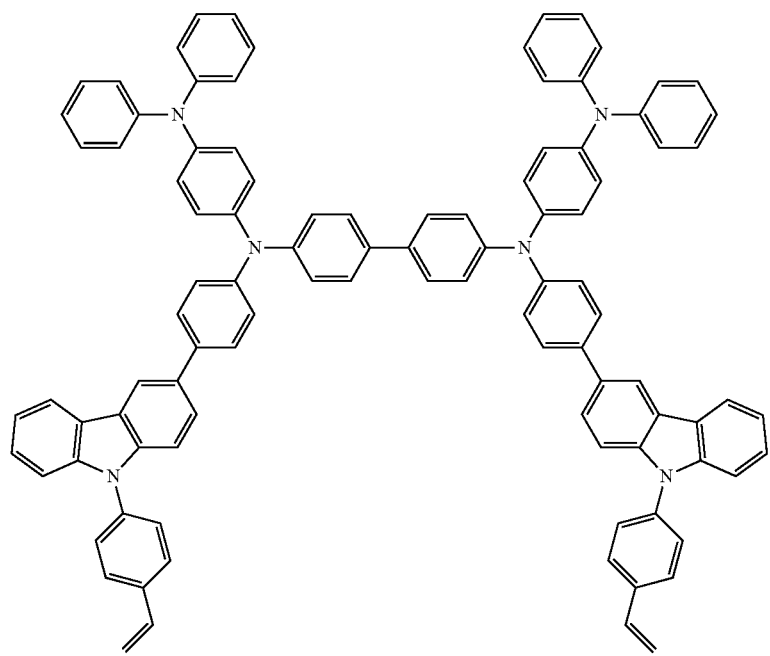

-continued

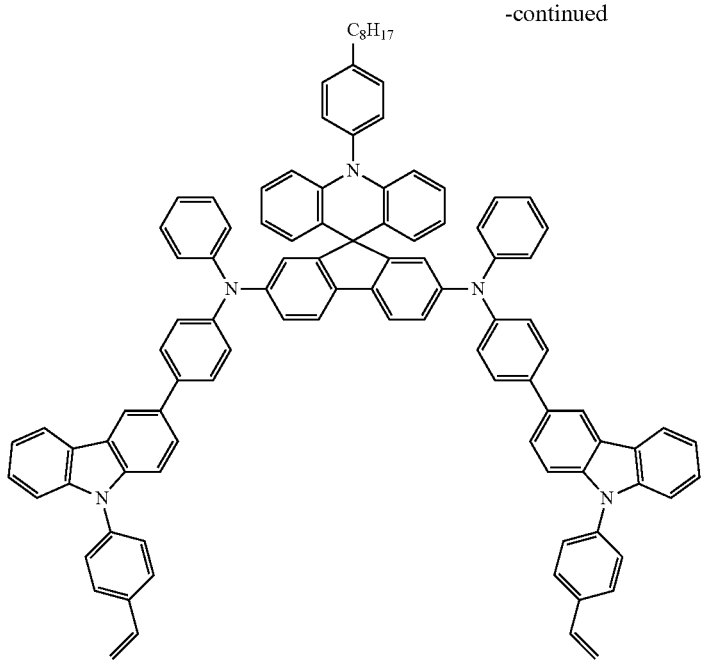

The present specification also provides a coating composition including the carbazole derivative described above.

In one embodiment of the present specification, the coating composition includes the carbazole derivative and a solvent.

In one embodiment of the present specification, the coating composition may further include one or two types of compounds selected from the group consisting of a compound introducing a thermocurable group or a photocurable group in the molecule and a polymer compound.

In one embodiment of the present specification, the coating composition may further include a compound introducing a thermocurable group or a photocurable group in the molecule. When the coating composition further includes a compound introducing a thermocurable group or a photocurable group in the molecule, the degree of curing of the coating composition may increase.

In one embodiment of the present specification, the compound introducing a thermocurable group or a photocurable group in the molecule has a molecular weight of 100 g/mol to 2,000 g/mol. In another embodiment of the present specification, the compound introducing a thermocurable group or a photocurable group in the molecule more preferably has a molecular weight of 100 g/mol to 1,000 g/mol.

In one embodiment of the present specification, the coating composition may further include a polymer compound. When the coating composition further includes a polymer compound, an ink property of the coating composition may be enhanced. In other words, the coating composition including a polymer compound is capable of providing proper viscosity to carry out coating or inkjet.

In one embodiment of the present specification, the coating composition has viscosity of 2 cP to 15 cP. Having such a viscosity range is useful in manufacturing a device.

In one embodiment of the present specification, the polymer compound has a molecular weight of 10,000 g/mol to 200,000 g/mol.

In one embodiment of the present specification, the polymer compound may further include a thermocurable group or a photocurable group.

In one embodiment of the present specification, the coating composition may be in a liquid state. The "liquid state" means being in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, cyclohexanone, isophorone, tetralone, decalone and acetylacetone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; tetraline, and the like, however, the solvent is not limited as long as the solvent is capable of dissolving or dispersing the carbazole derivative according to one embodiment of the present disclosure.

In another embodiment, the solvent may be used either alone as one type, or as a mixture of two or more types.

In one embodiment of the present specification, the coating composition may further include one, two or more types of additives selected from the group consisting of a thermal polymerization initiator and a photopolymerization initiator.

Examples of the thermal polymerization initiator may include peroxides such as methyl ethyl ketone peroxide, methyl isobutyl ketone peroxide, acetyl acetone peroxide, methyl cyclohexanone peroxide, cyclohexanone peroxide, isobutyryl peroxide, 2,4-dichlorobenzoyl peroxide, bis-3,5,5-trimethylhexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxy-isopropyl)benzene, t-butylcumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butyl peroxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butyl peroxy-3,5,5-trimethylhexate, t-butyl peroxybenzoate and di-t-butyl peroxy trimethyl adipate, or azo-based such as azobis isobutylnitrile, azobis dimethylvaleronitrile and azobis cyclohexylnitrile, but are not limited thereto.

Examples of the photopolymerization initiator may include acetophenone-based or ketal-based photopolymerization initiators such as diethoxyacetophenone, 2,2-dimethoxy-1,2-diphenylethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one and 1-phenyl-1,2-propanedion-2-(o-ethoxycarbonyl)oxime, benzoin ether-based photopolymerization initiators such as benzoin, benzoin methyl ether, benzoin ethyl ether, benzoin isobutyl ether and benzoin isopropyl ether, benzophenone-based photopolymerization initiators such as benzophenone, 4-hydroxybenzophenone, 2-benzoyl naphthalene, 4-benzoylbiphenyl, 4-benzoylphenyl ether, acrylated benzophenone and 1,4-benzoylbenzene, and thioxanthone-based photopolymerization initiators such as 2-isopropylthioxanthone, 2-chlorothioxanthone, 2,4-dimethylthioxanthone, 2,4-diethylthioxanthone and 2,4-dichlorothioxanthone. Examples of other photopolymerization initiators may include ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxy benzoyl)-2,4,4-trimethylpentylphosphine oxide, methylphenylglyoxyester, 9,10-phenanthrene, acridine-based compounds, triazine-based compounds, and imidazole-based compounds. In addition, those having an photopolymerization accelerating effect may be used either alone or as a combination with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

In one embodiment of the present specification, the coating composition does not further include a p-doping material.

In another embodiment, the coating composition further includes a p-doping material.

The p-doping material in the present specification means a material allowing a host material to have a p-semiconductor property. The p-semiconductor property means a property receiving or transferring holes at a highest occupied molecular orbital (HOMO) energy level, that is, a property of a material having high hole conductivity.

In one embodiment of the present specification, the p-doping material may be represented by a conductivity dopant of the following structures, however, the structure is not limited thereto. Including the conductivity dopant may mean a dopant increasing conductivity of an organic material layer formed using the carbazole derivative.

In one embodiment of the present specification, the conductivity dopant may be represented by any one of the following Chemical Formulae 14-1 to 14-10.

[Chemical Formula 14-1]

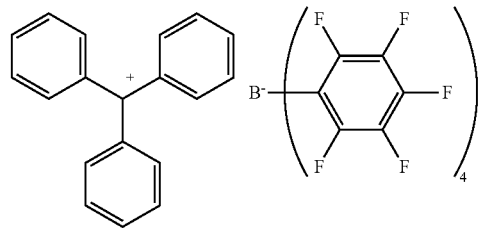

[Chemical Formula 14-2]

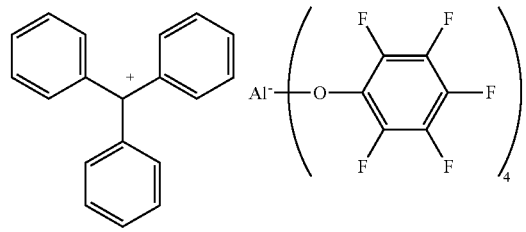

[Chemical Formula 14-3]

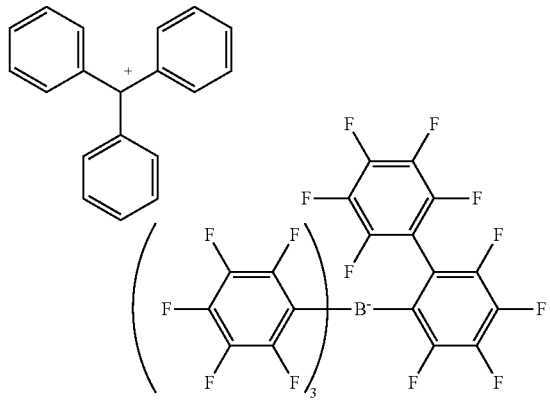

[Chemical Formula 14-4]

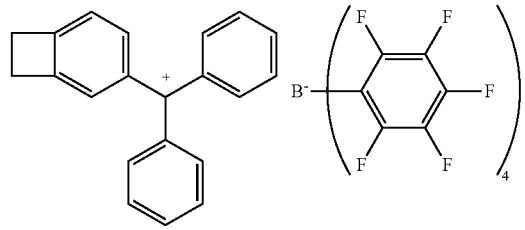

-continued

[Chemical Formula 14-5]

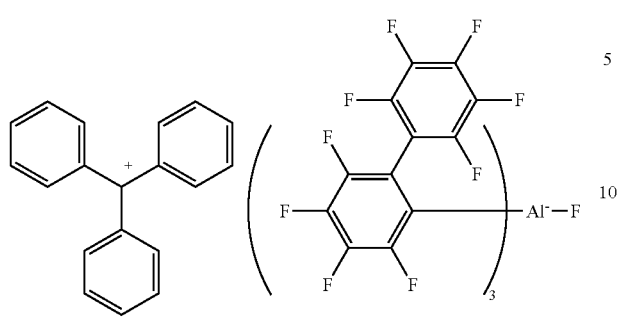

[Chemical Formula 14-6]

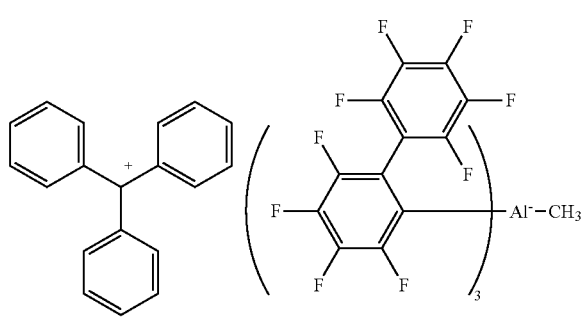

[Chemical Formula 14-7]

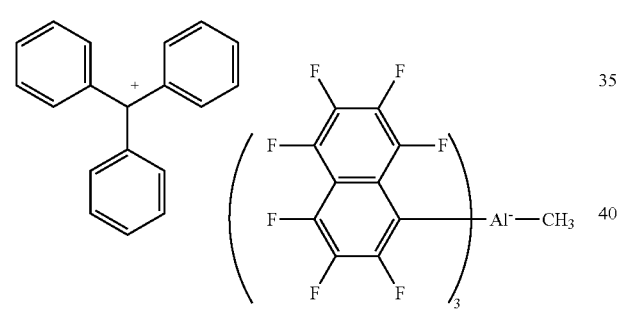

[Chemical Formula 14-8]

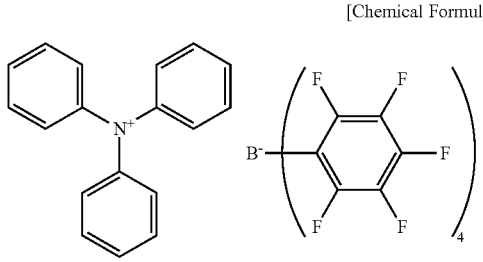

[Chemical Formula 14-9]

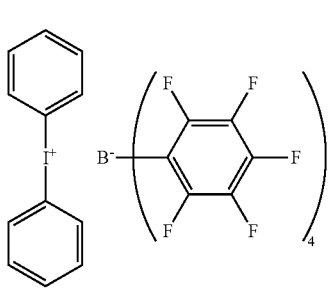

[Chemical Formula 14-10]

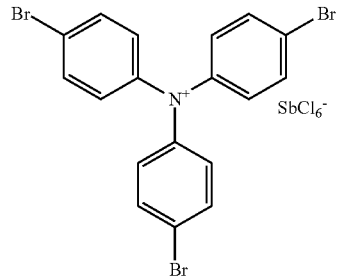

In another embodiment, the p-doping material may be a compound including a cyano group, for example, any one of compounds of the following structures, but is not limited thereto.

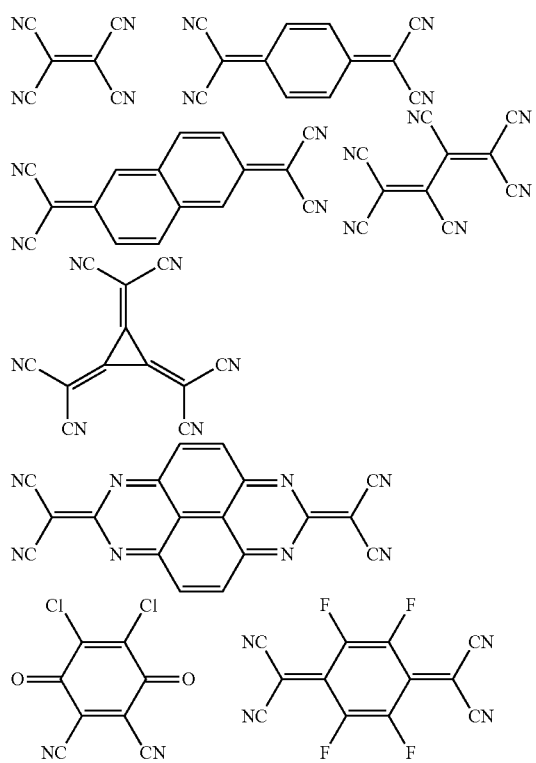

In another embodiment, polymer materials of polystyrene sulfonate (PSS) may be used as the p-doping material, however, the material is not limited thereto.

In another embodiment, the p-doping material may be $Ce(NH_4)_2(NO_3)_6$ or $[FeCp_2]PF_6$, but is not limited thereto.

In the present specification, the p-doping material is not limited as long as it is a material having p-semiconductor properties, and one, two or more types thereof may be used without limiting types thereof.

In one embodiment of the present specification, content of the p-doping material may be from 0% by weight to 50% by weight based on the carbazole derivative of Chemical Formula 1.

In one embodiment of the present specification, content of the p-doping material is from 0% by weight to 30% by weight based on the total solid content of the coating composition. In one embodiment of the present specification, content of the p-doping material is preferably from 1% by weight to 30% by weight based on the total solid content of the coating composition, and in another embodiment, content of the p-doping material is more preferably from 1% by weight to 10% by weight based on the total solid content of the coating composition.

In another embodiment, the coating composition may further include a monomer including a thermocurable group or a photocurable group; or a monomer including a terminal group capable of forming a polymer by heat. A molecular weight of the monomer including a thermocurable group or a photocurable group; or the monomer including a terminal group capable of forming a polymer by heat as above may be 2,000 g/mol or less.

As in one embodiment of the present specification, the curing temperature may be lowered when the coating composition further includes a monomer including a thermocurable group or a photocurable group; or a monomer including a terminal group capable of forming a polymer by heat, and the coating composition may be more preferably formed with similar structures that do not affect physical properties of the carbazole derivative of the present specification.

In one embodiment of the present specification, the coating composition has a molecular weight of 2,000 g/mol or less, and further includes a monomer including a thermocurable group or a photocurable group; or a monomer including a terminal group capable of forming a polymer by heat.

The monomer including a thermocurable group or a photocurable group; or the monomer including a terminal group capable of forming a polymer by heat may mean a monomer in which aryl of phenyl, biphenyl, fluorene or naphthalene; arylamine; or carbazole is substituted with a thermocurable group, a photocurable group or a terminal group capable of forming a polymer by heat.

In another embodiment, the coating composition has viscosity of 2 cP to 15 cP.

The present specification also provides an organic light emitting device formed using the coating composition.

In one embodiment of the present specification, the organic light emitting device includes a cathode; an anode; and one or more organic material layers provided between the cathode and the anode, and by being formed using the coating composition, one or more layers of the organic material layers include a cured material of the coating composition. A cured material of the coating composition means a cured state obtained by heat treating or light treating the coating composition.

In one embodiment of the present specification, the organic material layer including a cured material of the coating composition is a hole transfer layer, a hole injection layer or a layer carrying out hole transfer and hole injection at the same time.

In another embodiment, the organic material layer formed using the coating composition is a light emitting layer.

In another embodiment, the organic material layer including a cured material of the coating composition is a light emitting layer, and the light emitting layer includes the carbazole derivative as a host of the light emitting layer.

In one embodiment of the present specification, the organic light emitting device further includes one, two or more layers selected from the group consisting of a hole injection layer, a hole transfer layer, an electron transfer layer, an electron injection layer, an electron blocking layer and a hole blocking layer.

In another embodiment, the organic light emitting device may be an organic light emitting device having a structure consecutively laminating an anode, one or more organic material layers and a cathode on a substrate (normal type).

In another embodiment, the organic light emitting device may be an organic light emitting device having an inverted structure consecutively laminating a cathode, one or more organic material layers and an anode on a substrate (inverted type).

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

For example, a structure of an organic light emitting device according to one embodiment of the present specification is illustrated in FIG. 1.

FIG. 1 illustrates a structure of an organic light emitting device in which an anode (201), a hole injection layer (301), a hole transfer layer (401), a light emitting layer (501), an electron transfer layer (601) and a cathode (701) are consecutively laminated on a substrate (101).

In FIG. 1, the hole injection layer (301), the hole transfer layer (401) and the light emitting layer (501) are formed using the coating composition including the carbazole derivative.

FIG. 1 is a diagram illustrating an organic light emitting device, and the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition including the carbazole derivative.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

The present specification also provides a method for manufacturing an organic light emitting device formed using the coating composition.

Specifically, in one embodiment of the present specification, the method includes preparing a substrate; forming a cathode or an anode on the substrate; forming one or more organic material layers on the cathode or the anode; and forming an anode or a cathode on the organic material layers, wherein one or more layers of the organic material layers are formed using the coating composition.

In one embodiment of the present specification, the organic material layer formed using the coating composition is formed using spin coating.

In another embodiment, the organic material layer formed using the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of organic material layers formed using the coating composition includes coating the coating composition on the cathode or the anode; and heat treating or light treating the coated coating composition.

In one embodiment of the present specification, a heat treatment temperature in the heat treatment is from 85° C. to 300° C.

In another embodiment, a heat treatment time in the heat treatment may be from 1 minute to 1 hour.

In one embodiment of the present specification, when the coating composition does not include additives, crosslinking is preferably progressed through heat treatment at a temperature of 100° C. to 300° C., and crosslinking is more preferably progressed at a temperature of 150° C. to 250° C. In addition, the coating composition of the present specification may further include an initiator, but it is more preferable not to use an initiator.

When the heat treatment or the light treatment is included in the forming of organic material layers formed using the coating composition, an organic material layer including a thin-filmed structure by a plurality of the carbazole derivatives included in the coating composition forming crosslinkage may be provided. In this case, when another layer is laminated on the surface of the organic material layer formed using the coating composition, dissolution caused by a solvent, or morphological influences or decomposition may be prevented.

Accordingly, when an organic material layer formed using the coating composition is formed including the heat treatment or the light treatment, resistance for a solvent increases, and multiple layers may be formed by repeatedly carrying out solution deposition and crosslinking methods, and as a result, a lifespan property of a device may be enhanced by increasing stability.

In one embodiment of the present specification, the coating composition including the carbazole derivative may use a coating composition mixed and dispersed to a polymer bonding agent.

As the polymer bonding agent in one embodiment of the present specification, those that do not extremely inhibit charge transfer are preferred, and those that do not exhibit strong absorption for visible light are preferably used. Examples of the polymer bonding agent include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

By the carbazole derivative according to one embodiment of the present specification including carbazole and an amine group, the carbazole derivative may be included alone in the organic material layer, or the coating composition including the carbazole derivative may be progressed to a thin film through heat treatment or light treatment, or may be included as a copolymer using a coating composition mixed with other monomers. In addition, the coating composition may be included as a copolymer or included as a mixture by using a coating composition mixed with other polymers.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present specification, the heterocyclic compound may be included in organic solar cells or organic transistors in addition to organic light emitting devices.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

Compounds having the structure of Chemical Formula 1 may be prepared using the following starting materials or intermediate compounds, but are not limited thereto.

[Chemical Formula A-1]

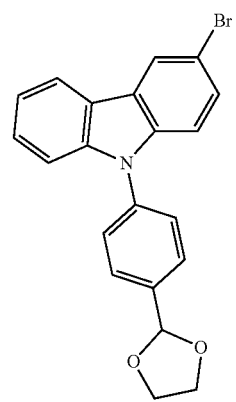

[Chemical Formula A-2]
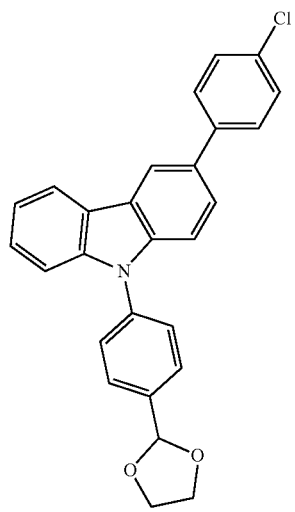
[Chemical Formula A-5]
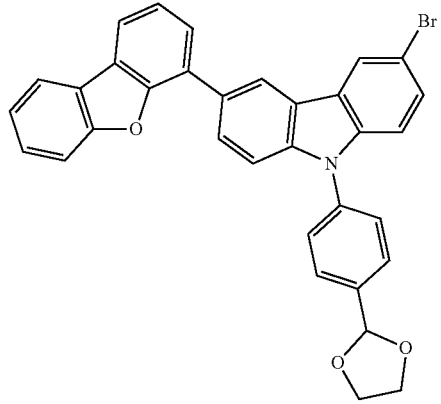
[Chemical Formula A-3]
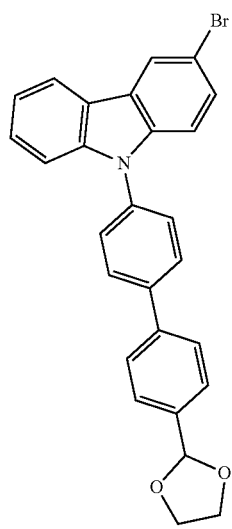
[Chemical Formula A-6]
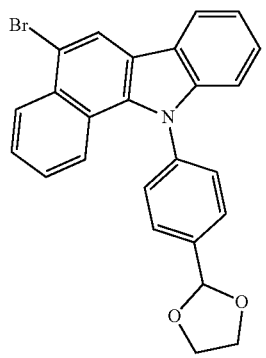
[Chemical Formula A-4]
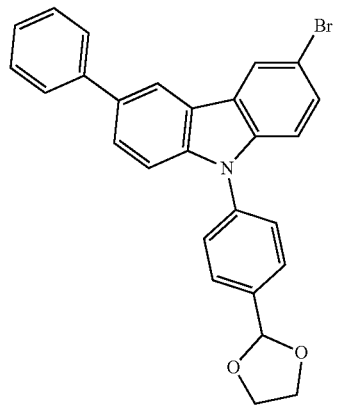
[Chemical Formula A-7]
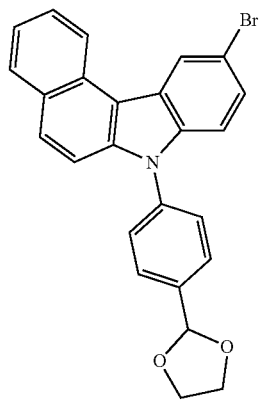

[Chemical Formula B-1]
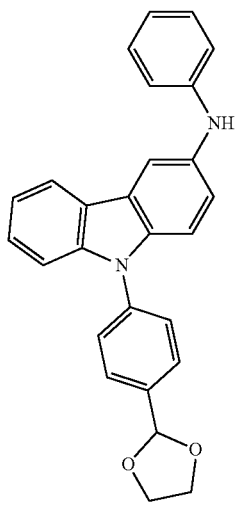
[Chemical Formula B-2]
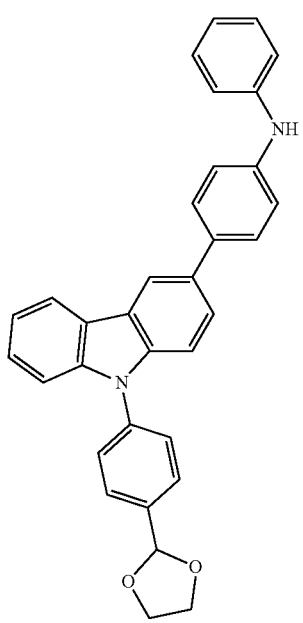
[Chemical Formula B-3]
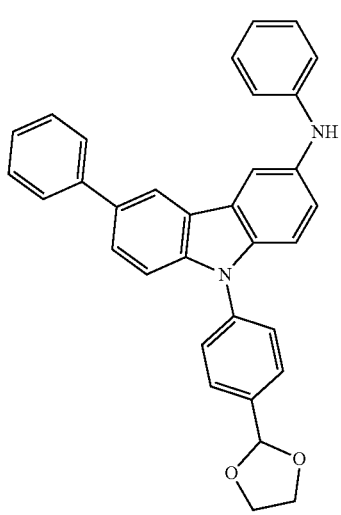
[Chemical Formula B-4]
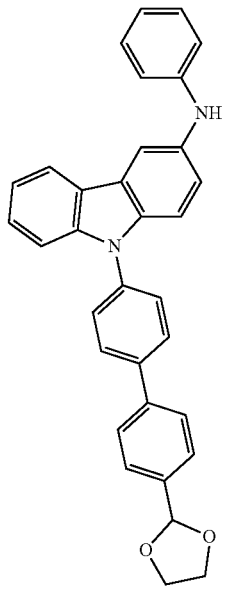
[Chemical Formula B-5]
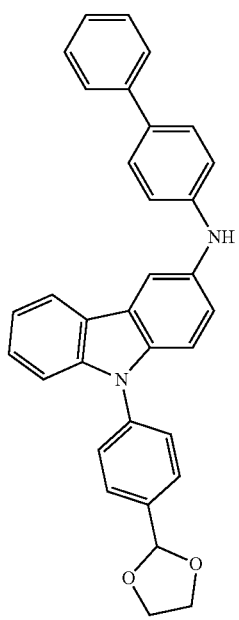

[Chemical Formula B-6]
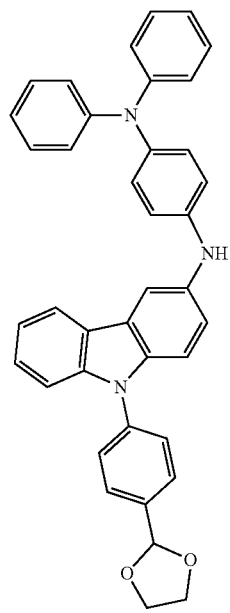
[Chemical Formula B-8]
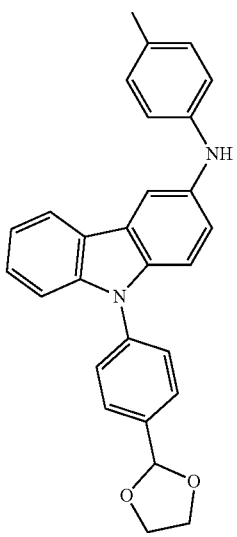
[Chemical Formula B-7]
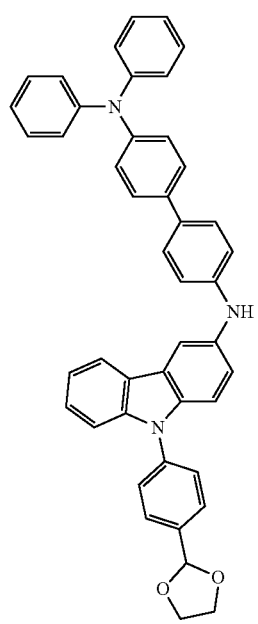
[Chemical Formula B-9]
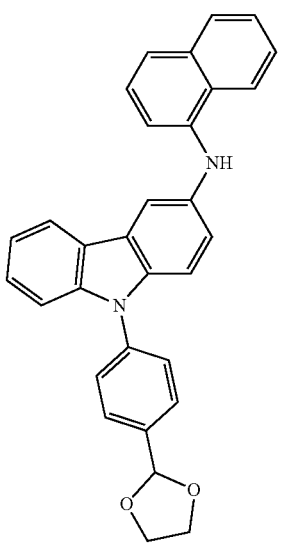

[Chemical Formula B-10]

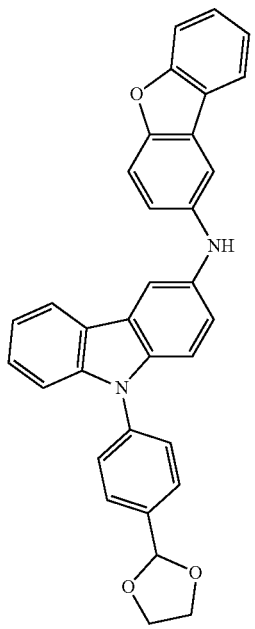

[Chemical Formula B-11]

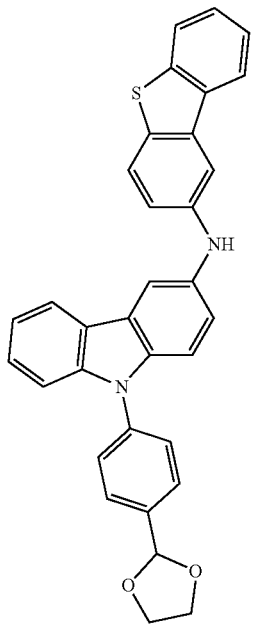

[Chemical Formula B-12]

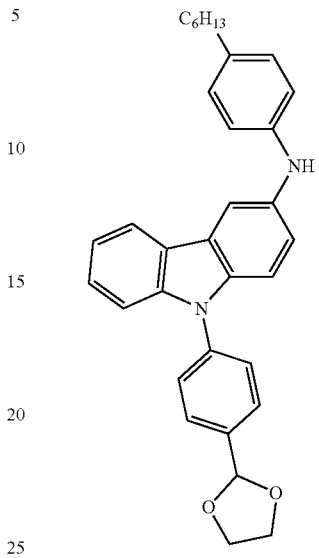

An aryl halide compound capable of reacting with the arylamine group includes the following types, and although only a bromo group is provided, the compound is not limited thereto. In addition, compounds below Chemical Formula C-1 correspond to an A skeleton in the general formula structure.

In addition, Br in the compounds below the following Chemical Formula C-1 may be substituted with other substituents such as Cl, OTf or OTs, however, the substitution is not limited thereto.

[Chemical Formula C-1]

[Chemical Formula C-2]

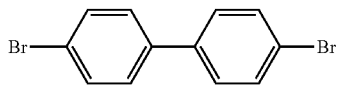

[Chemical Formula C-3]

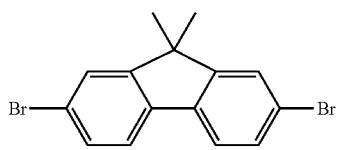

[Chemical Formula C-4]

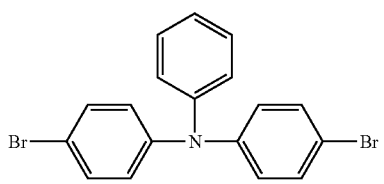

-continued
[Chemical Formula C-5]
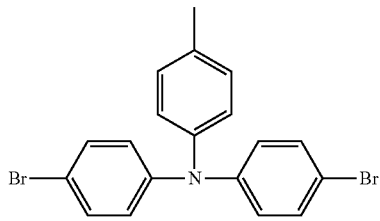
[Chemical Formula C-6]
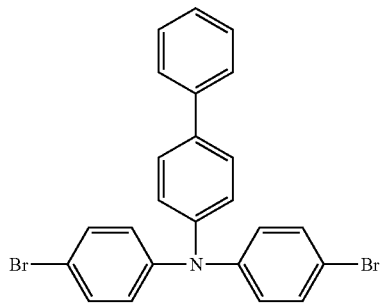
[Chemical Formula C-7]
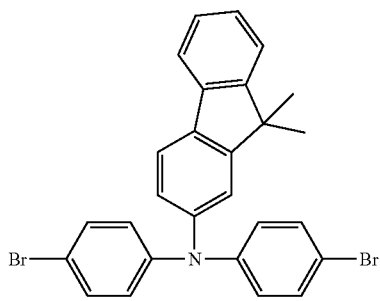
[Chemical Formula C-8]
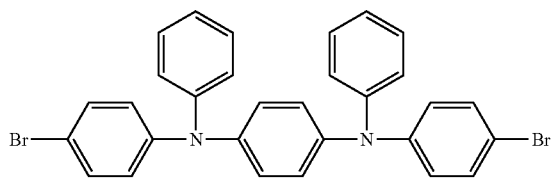
[Chemical Formula C-9]
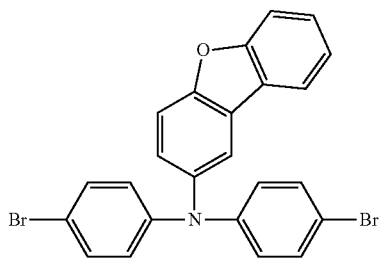
[Chemical Formula C-10]
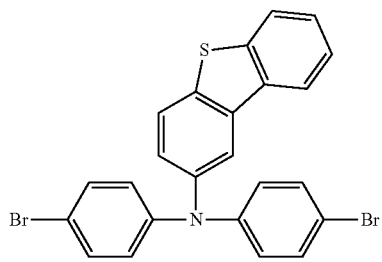
[Chemical Formula C-11]
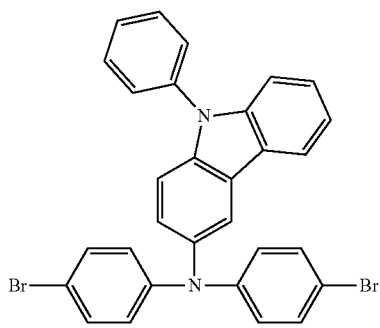
[Chemical Formula C-12]
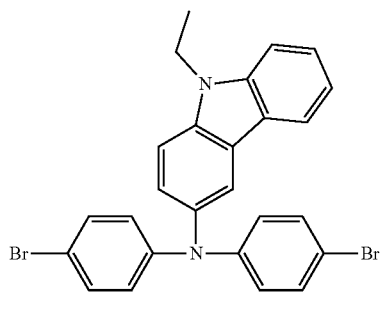
[Chemical Formula C-13]
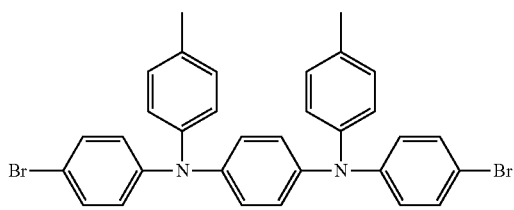
[Chemical Formula C-14]
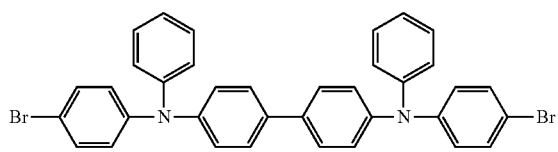

-continued
[Chemical Formula C-15]
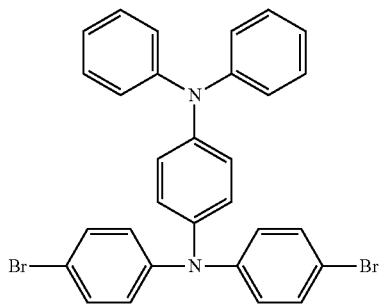
[Chemical Formula C-16]
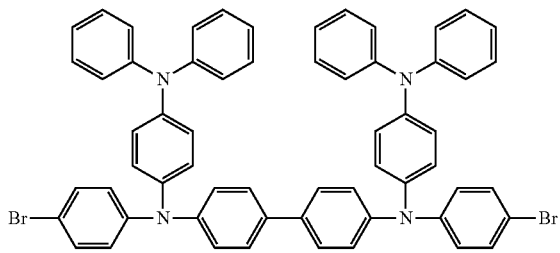
[Chemical Formula C-17]
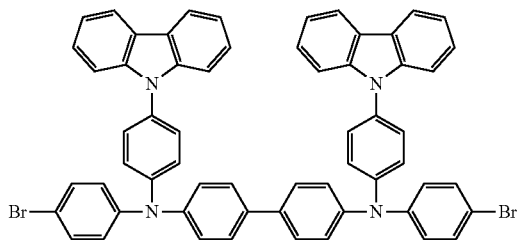
[Chemical Formula C-18]
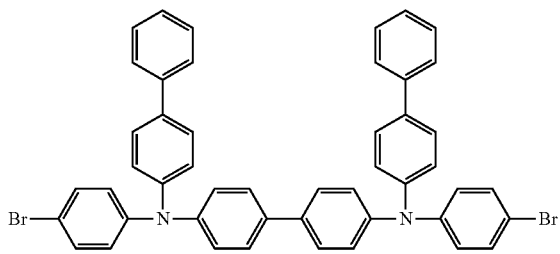
[Chemical Formula C-19]
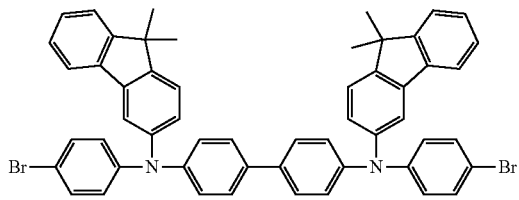
[Chemical Formula C-20]
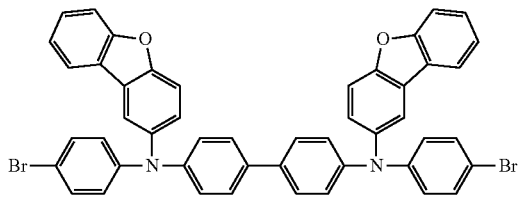
[Chemical Formula C-21]
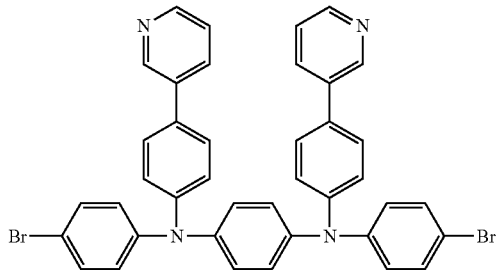
[Chemical Formula C-22]
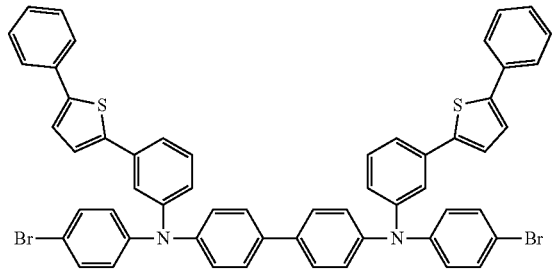
[Chemical Formula C-23]
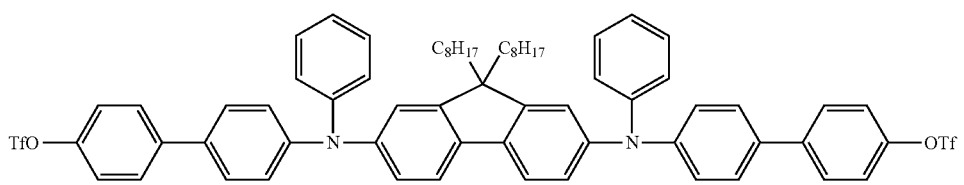

-continued
[Chemical Formula C-24]
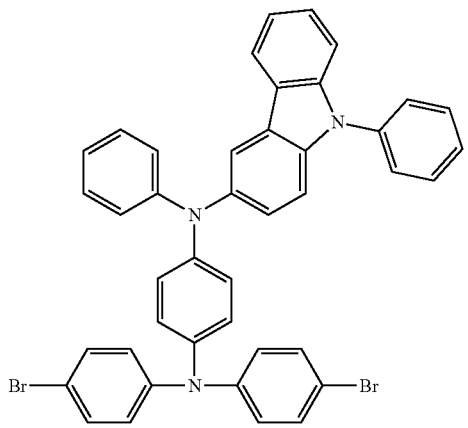
[Chemical Formula C-25]
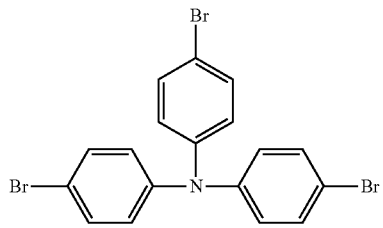
[Chemical Formula C-26]
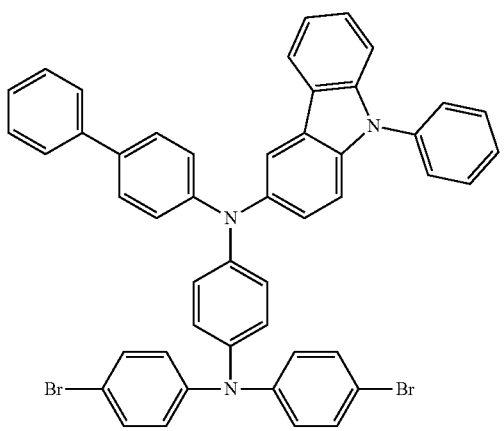
[Chemical Formula C-27]
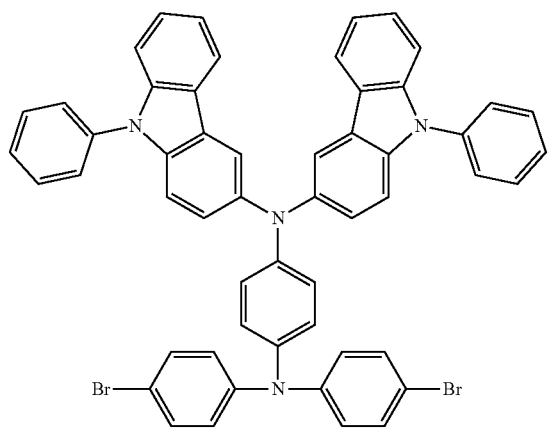
[Chemical Formula C-28]
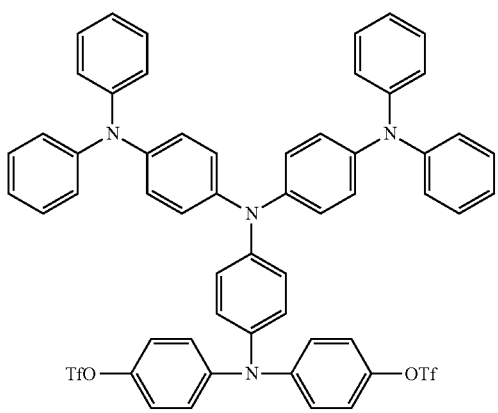
[Chemical Formula C-29]
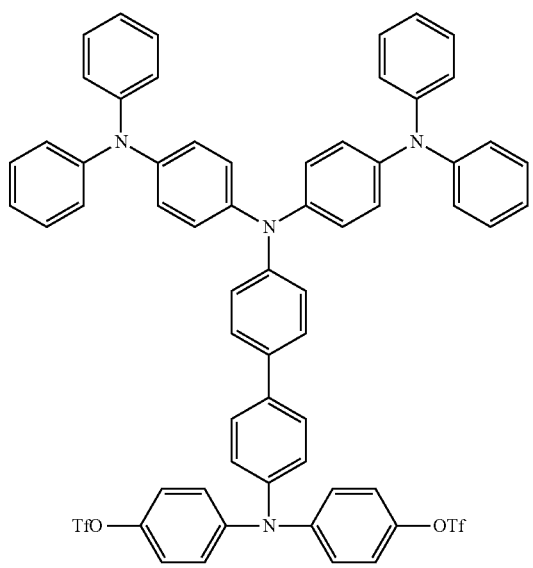

[Chemical Formula C-30]
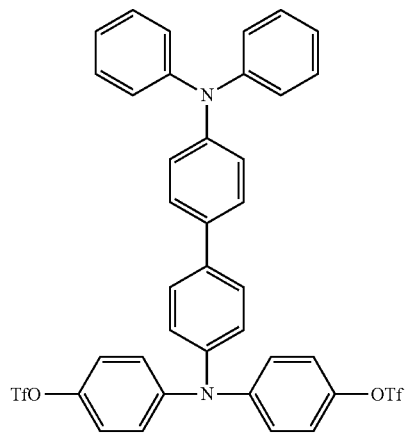
[Chemical Formula C-31]
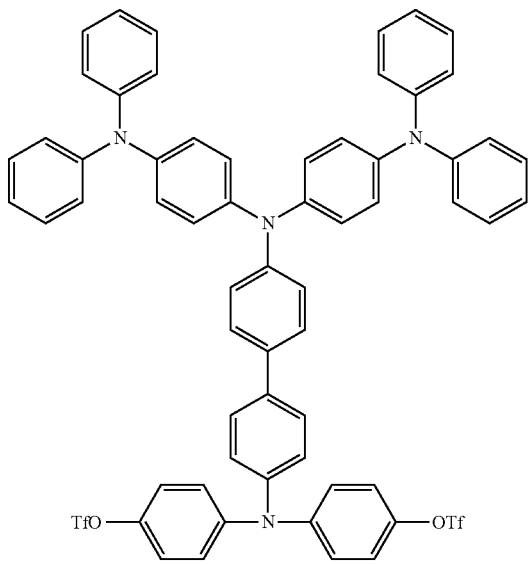
[Chemical Formula C-32]
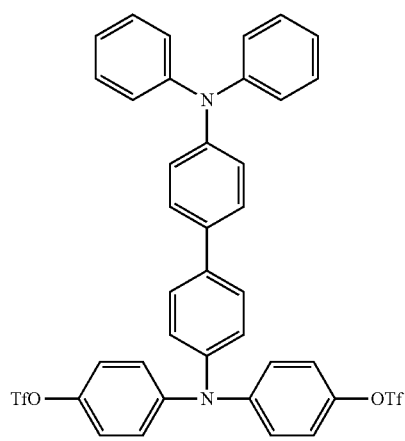
[Chemical Formula C-33]
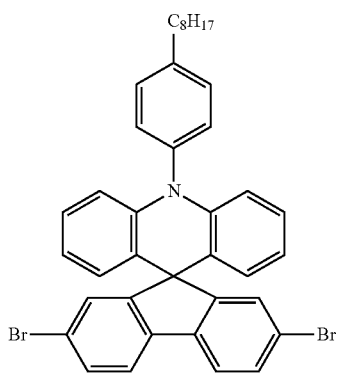
[Chemical Formula C-34]
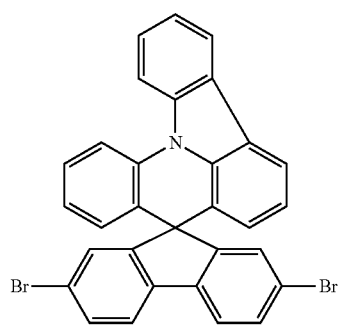

Preparation Example 1-1-1. Preparation of Chemical Formula 1-1-1

<Preparation of Chemical Formula B-1>

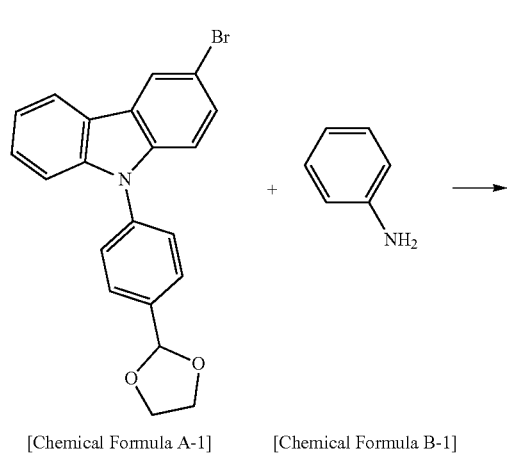

[Chemical Formula A-1]   [Chemical Formula B-1]

After dissolving a chemical formula of 9-(4-(1,3-dioxolan-2-yl)phenyl)-3-bromo-9H-carbazole (10 g, 25.4 mmol) and aniline (4.73 g, 50.8 mmol) in 200 ml of xylene, sodium t-butoxide (12.2 g, 127 mmol), bis(dibenzylideneacetone)palladium(0) (0.13 g, 0.23 mmol) and a 50 wt % tri-tertiary-butylphosphine toluene solution (0.11 ml, 0.23 mmol) were added thereto, and the result was refluxed for 5 hours under nitrogen atmosphere.

Distilled water was added to the reaction solution to terminate the reaction, and the organic layer was extracted. The result was column separated using a normal-hexane/tetrahydrofuran=6/1 solvent, stirred with ethyl alcohol (EtOH) and hexane, and then filtered and vacuum dried to obtain Chemical Formula B-1 (6.71 g, yield 65%). MS: [M+H]$^+$=407

<Preparation of Chemical Formula C-1-1>

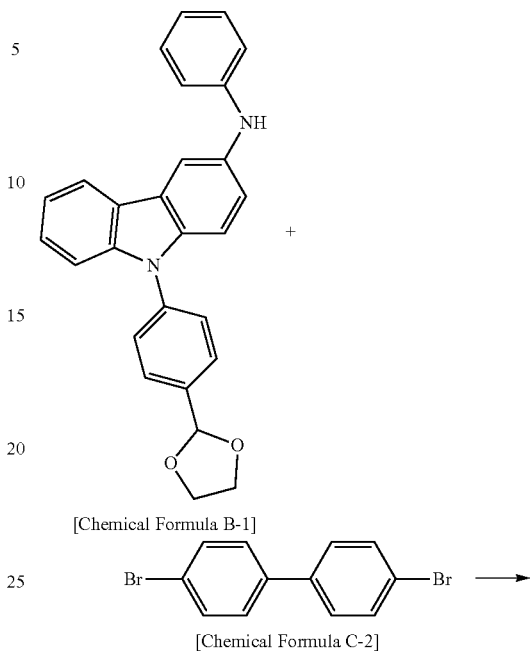

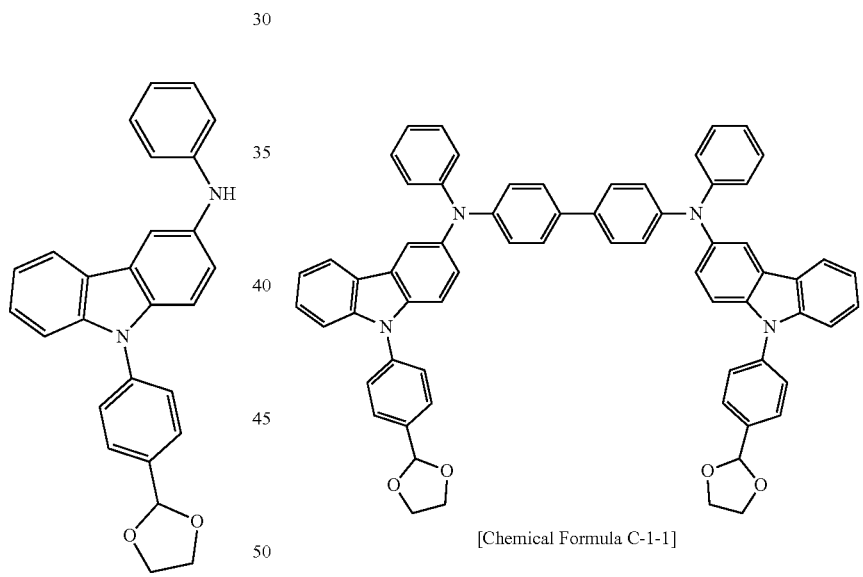

[Chemical Formula C-1-1]

After dissolving 4,4'-dibromo-1,1'-biphenyl (1.93 g, 6.2 mmol), Chemical Formula C-2, and 9-(4-(1,3-dioxolan-2-yl)phenyl)-N-phenyl-9H-carbazol-3-amine (10 g, 24.6 mmol), Chemical Formula B-1, in 200 ml of xylene, sodium t-butoxide (4.76 g, 49.6 mmol), bis(dibenzylideneacetone)palladium(0) (0.065 g, 0.115 mmol) and a 50 wt % tri-tertiary-butylphosphine toluene solution (0.055 ml, 0.115 mmol) were added thereto, and the result was refluxed for 5 hours under nitrogen atmosphere.

Distilled water was added to the reaction solution to terminate the reaction, and the organic layer was extracted. The result was column separated using a normal-hexane/tetrahydrofuran=6/1 solvent, stirred with ethyl alcohol (EtOH) and hexane, and then filtered and vacuum dried to obtain Chemical Formula C-1-1 (4.74 g, yield 46%). MS: [M+H]$^+$=963

<Preparation of Chemical Formula D-1-1>
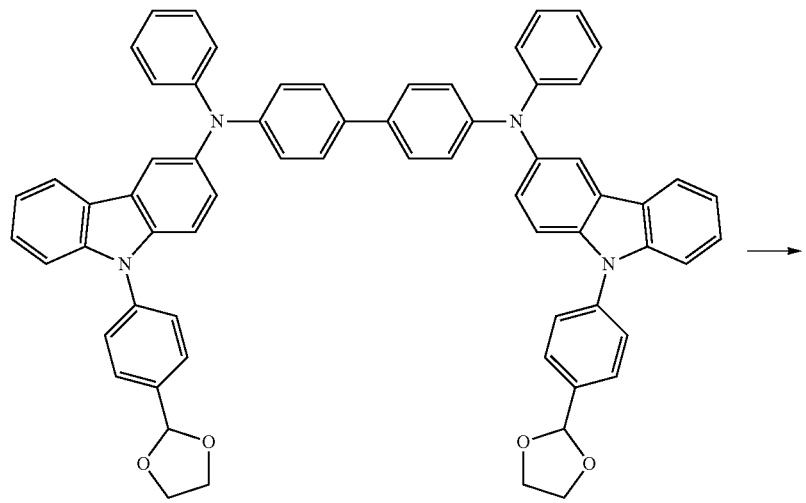
[Chemical Formula C-1-1]
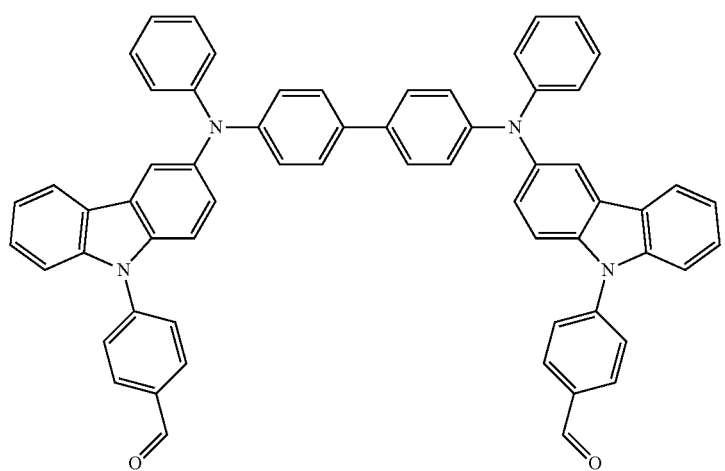
[Chemical Formula D-1-1]

After dissolving Chemical Formula C-1-1 (4.74 g, 4.92 mmol) in THF, 20 mL of 2 N HCl was added thereto, the result was stirred, and the organic material layer was extracted with $CH_2Cl_2$. The result was dried with anhydrous magnesium sulfate, filtered and vacuum distilled, then column separated using a normal-hexane/tetrahydrofuran=6/1 solvent, and then stirred with $CH_2Cl_2$ and ethyl alcohol (EtOH) to obtain Chemical Formula D-1-1 (3.7 g, yield 86%). MS: $[M+H]^+=875$ <Preparation of Chemical Formula 1-1-1>

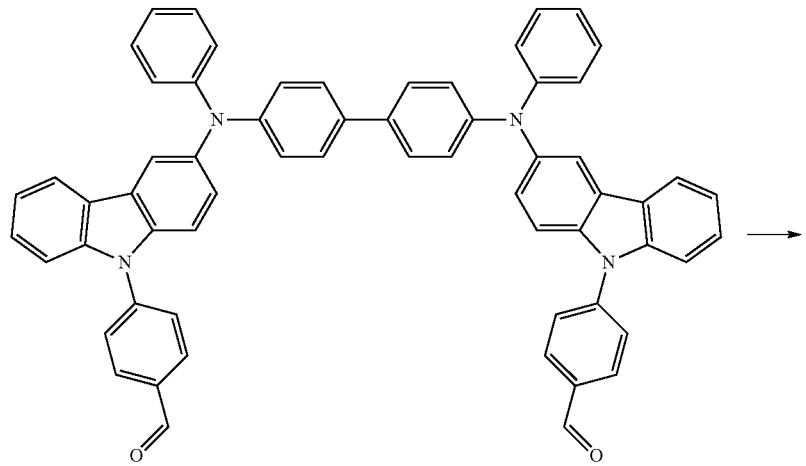

[Chemical Formula D-1-1]

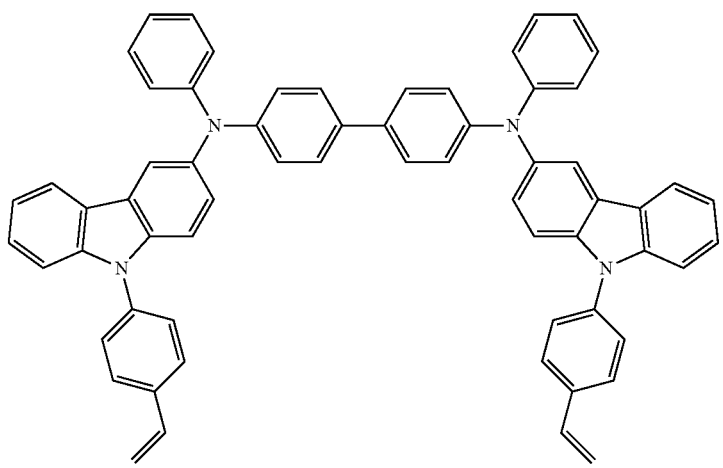

[Chemical Formula 1-1-1]

After dissolving (bromomethyl)triphenylphosphonium bromide (2.55 g, 5.85 mmol) in 100 mL of tetrahydrofuran (THF), 1 eq. of n-butyllithium (n-BuLi)(2.5 M in HEX, 2.34 mL, 5.85 mmol) was added thereto at −78° C., and the result was stirred for 20 minutes. After raising the reaction temperature to 0° C., Chemical Formula D-1-1 (1.75 g, 2.0 mmol) was introduced to the reaction material, and the result was stirred for 1 hour at the same temperature. Distilled water was added to the reaction solution to terminate the reaction, and the organic layer was extracted. The reaction solution was concentrated, dissolved in methylene chloride (MC), and then recrystallized with ethyl alcohol (EtOH) to obtain Chemical Formula 1-1-1 (0.73 g, yield 42%). MS: $[M+H]^+=871$. Results of an MS spectrum, a 1H NMR spectrum and a DSC measurement of Chemical Formula 1-1-1 are shown in FIGS. 2 to 4, respectively.

Preparation Example 1-2-1. Preparation of Chemical Formula 1-2-1

<Preparation of Chemical Formula D-2-1>

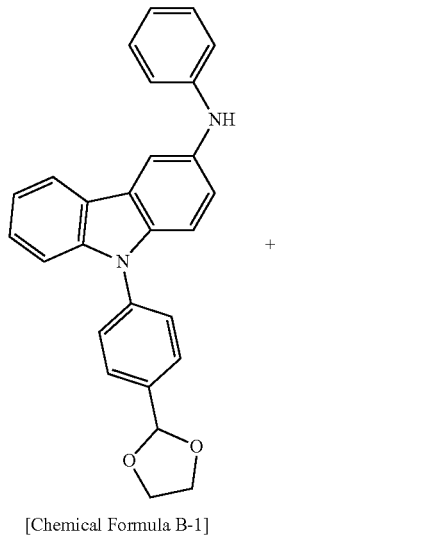

[Chemical Formula B-1]

+

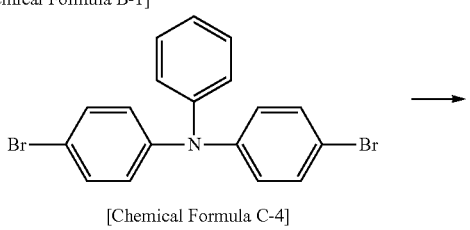

[Chemical Formula C-4]

→

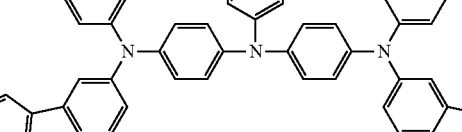

[Chemical Formula C-1-18]

Chemical Formula C-1-18 was obtained in the same manner as in the preparation example of Chemical Formula C-1-1 of the preparation example of Chemical Formula 1-1-1, except that 4-bromo-N-(4-bromophenyl)-N-phenylaniline was used instead of 4,4'-dibromobiphenyl.

Chemical Formula D-2-1 was obtained in the same manner as in the preparation example of Chemical Formula D-1-1 of the preparation example of Chemical Formula 1-1-1, except that Chemical Formula C-1-18 was used instead of Chemical Formula C-1-1.

MS: [M+H]$^+$=1054

<Preparation of Chemical Formula 1-2-1>

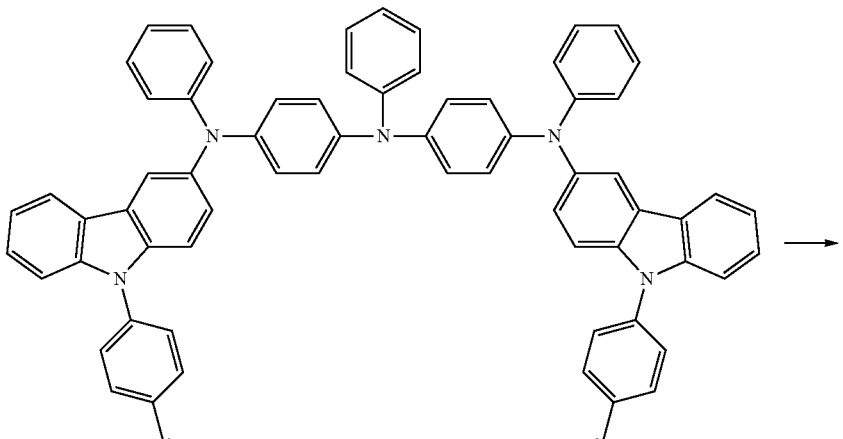

[Chemical FormulaD-2-1]

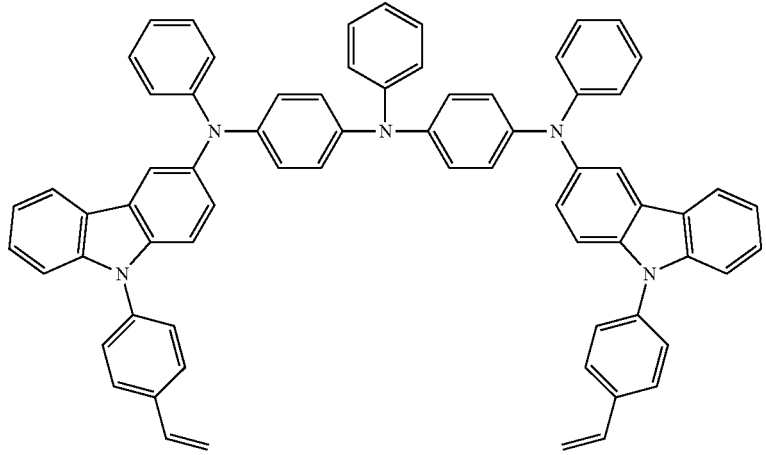

[Chemical Formula 1-2-1]

After dissolving (bromomethyl)triphenylphosphonium bromide (2.55 g, 5.85 mmol) in 100 mL of tetrahydrofuran (THF), 1 eq. of n-butyllithium (n-BuLi)(2.5 M in HEX, 2.34 mL, 5.85 mmol) was added thereto at −78° C., and the result was stirred for 20 minutes. After raising the reaction temperature to 0° C., Chemical Formula D-2-1 (2 g, 1.95 mmol) was introduced to the reaction material, and the result was stirred for 1 hour at the same temperature. Distilled water was added to the reaction solution to terminate the reaction, and the organic layer was extracted. The reaction solution was concentrated, dissolved in methylene chloride (MC), and then recrystallized with ethyl alcohol (EtOH) to obtain Chemical Formula 1-2-1 (1.28 g, yield 64%). MS: $[M+H]^+$= 962

Preparation Example 1-3-1. Preparation of Chemical Formula 1-3-1

<Preparation of Chemical Formula C-3-1>

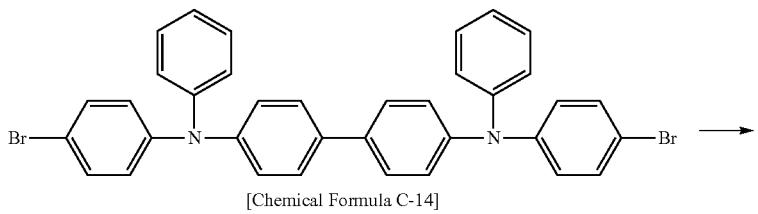

[Chemical Formula C-14]

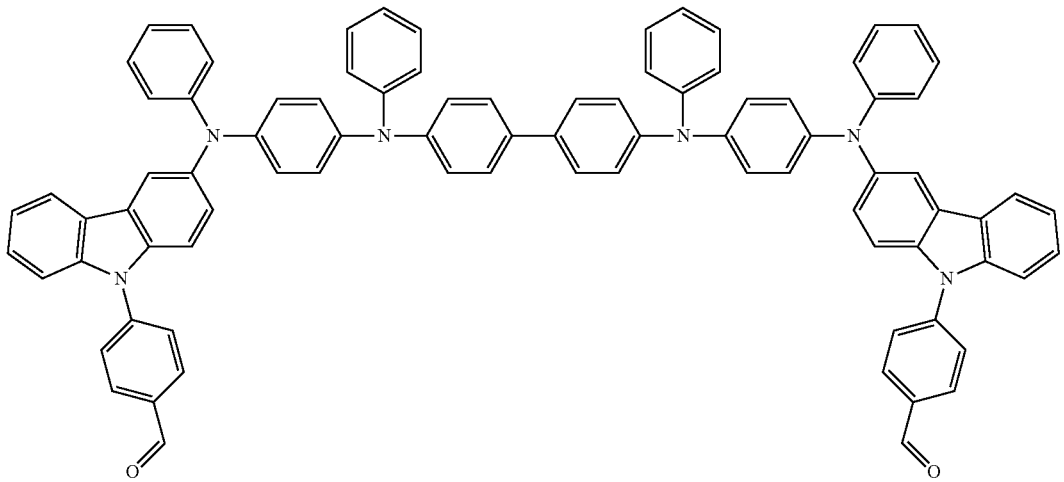

[Chemical Formula C-3-1]

After dissolving 4-bromo-N-(4-bromophenyl)-N-phenylaniline (2.5 g, 6.2 mmol), Chemical Formula C-14, and 9-(4-(1,3-dioxolan-2-yl)phenyl)-N-phenyl-9H-carbazol-3-amine (10 g, 24.6 mmol), Chemical Formula B-1, in 200 ml of xylene, sodium t-butoxide (4.76 g, 49.6 mmol), bis(dibenzylideneacetone)palladium(0) (0.065 g, 0.115 mmol) and a 50 wt % tri-tertiary-butylphosphine toluene solution (0.055 ml, 0.115 mmol) were added thereto, and the result was refluxed for 5 hours under nitrogen atmosphere.

Distilled water was added to the reaction solution to terminate the reaction, and the organic layer was extracted. The result was recrystallized with THF and ethyl alcohol (EtOH), and filtered and vacuum dried to obtain Chemical Formula C-3-1 (4.74 g, yield 46%). MS: $[M+H]^+=1209$ <Preparation of Chemical Formula 1-3-1>

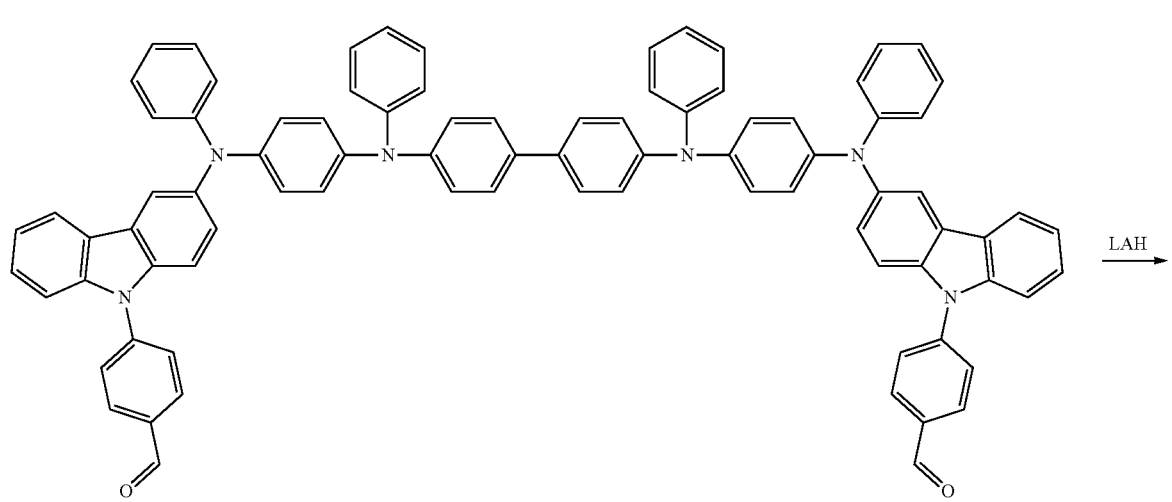

[Chemical Formula C-3-1]

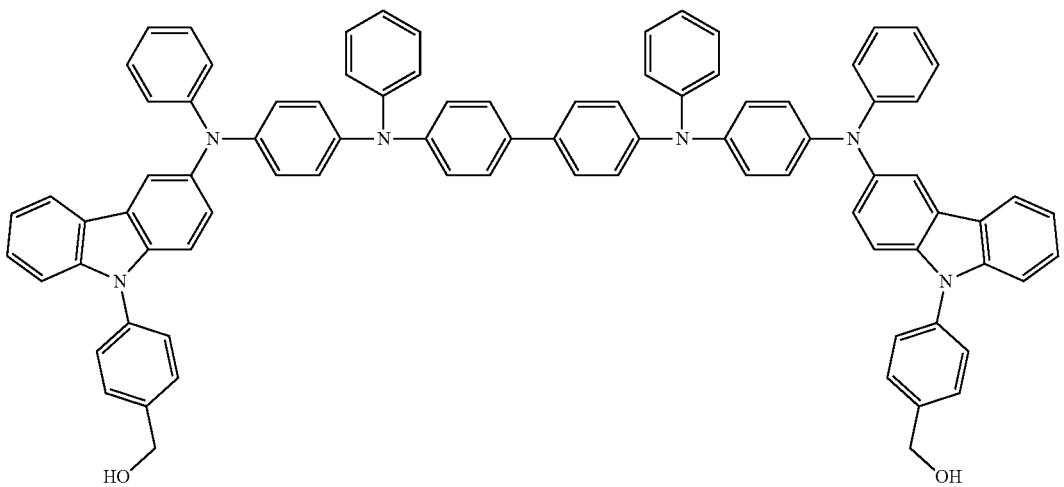

[Chemical Formula D-3-1]

After adding lithium aluminum hydride (LiAlH$_4$, 0.31 g, 8.25 mmol) was added to 120 mL of THF and lowering the temperature of the reaction material to 0° C., a compound of Chemical Formula C-3-1 (2 g, 1.65 mmol) was slowly added to the reaction material. After stirring the result for 4 hours at 0° C., the reaction was terminated using an aqueous sodium hydroxide (NaOH) solution, and the result was stirred for 12 hours at room temperature. The undissolved solid salts were filtered and removed, and then the organic solvent was removed using a rotary evaporator. The residue was dissolved in THF and ethanol was added thereto for precipitation to obtain Chemical Formula D-3-1 (1.6 g, yield 79.9%). MS: [M+H]$^+$=1214

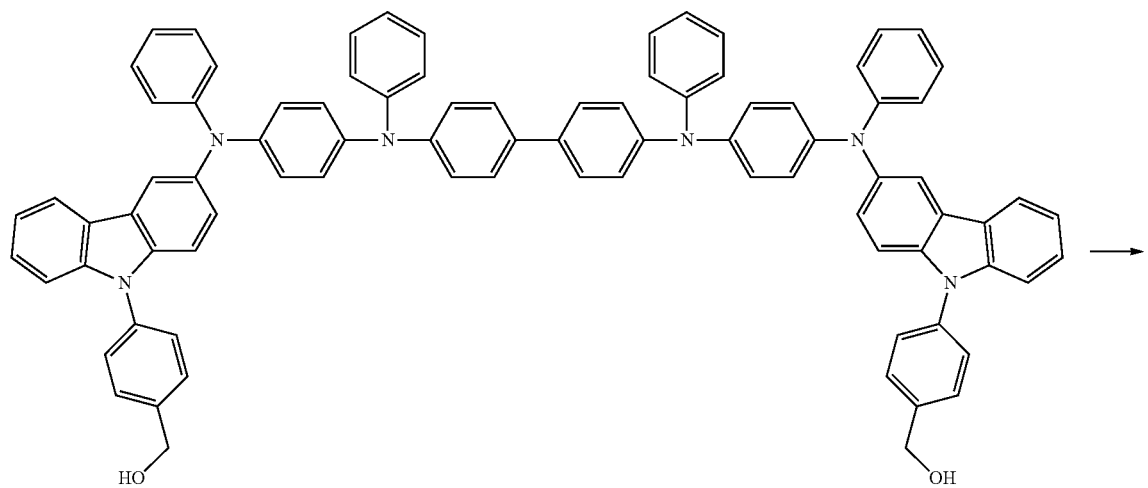

[Chemical Formula D-3-1]

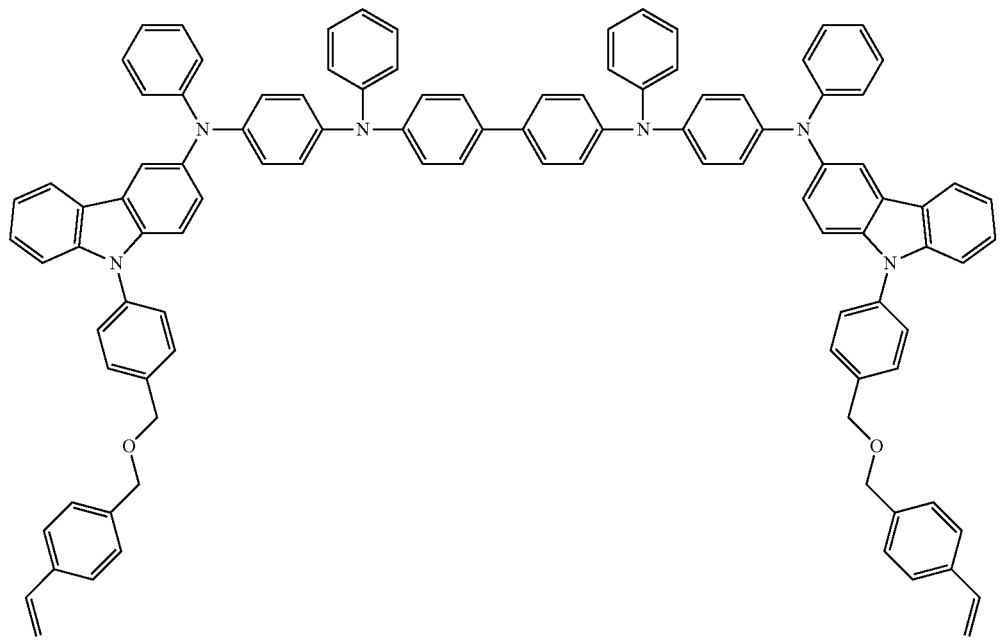

[Chemical Formula 1-3-1]

After dissolving a compound of Chemical Formula D-3-1 (1.6 g, 1.32 mmol) in 50 mL of anhydrous dimethylformamide (DMF), the temperature was lowered to 0° C. Sodium hydride (NaH, 60 wt %, 0.3 g, 7.6 mmol) was added thereto, the result was stirred for 1 hour, and then 4-vinylbenzyl chloride (0.78 mL, 5.5 mmol) was added thereto. After stirring the result for 6 hours at 70° C., water was added thereto to terminate the reaction, and the solids were dropped. After column purification, the mixture was recrystallized using dichloromethane and hexane to obtain Chemical Formula 1-3-1 (1.3 g, yield 70%).

Preparation Example 1-4-1. Preparation of Chemical Formula 1-4-1

<Preparation of Chemical Formula B-4-1>

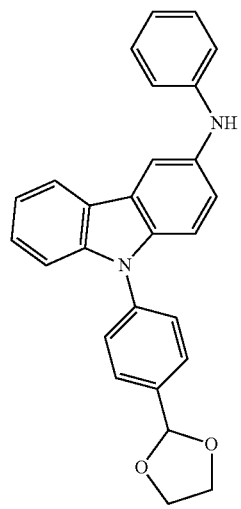

[Chemical Formula B-1]

+

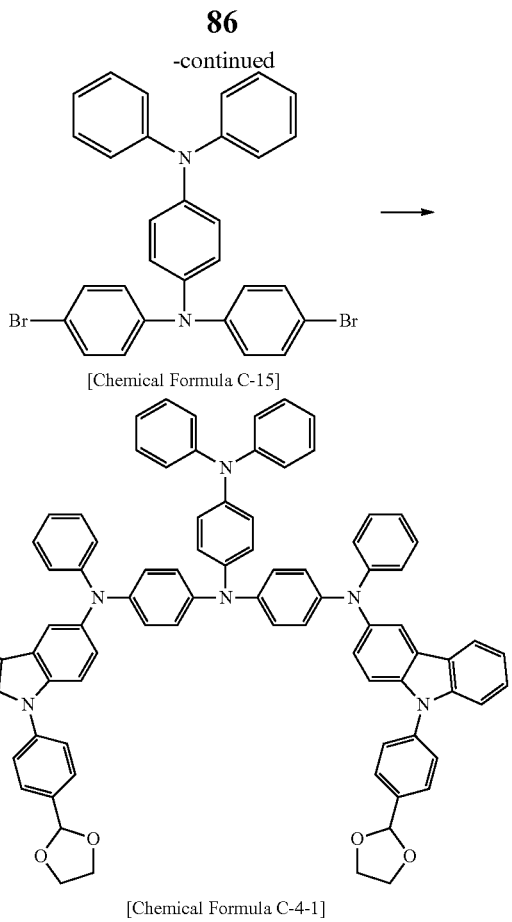

[Chemical Formula C-15]

[Chemical Formula C-4-1]

<Preparation of Chemical Formula C-4-1>

Chemical Formula C-4-1 was obtained in the same manner as in the preparation example of Chemical Formula 1-1-1, except that Chemical Formula C-15 was used instead of Chemical Formula C-2. MS: [M+H]$^+$=1222

<Preparation of Chemical Formula D-4-1>

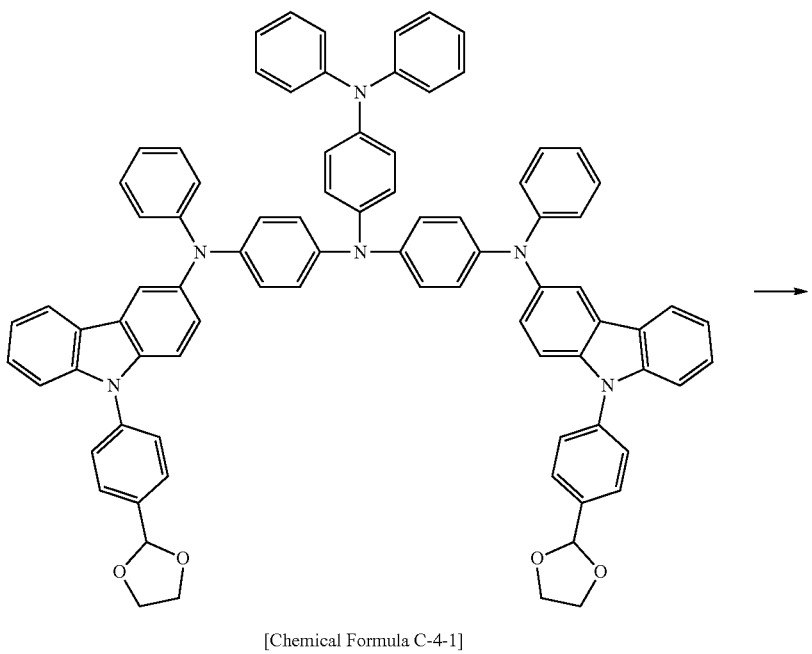

[Chemical Formula C-4-1]

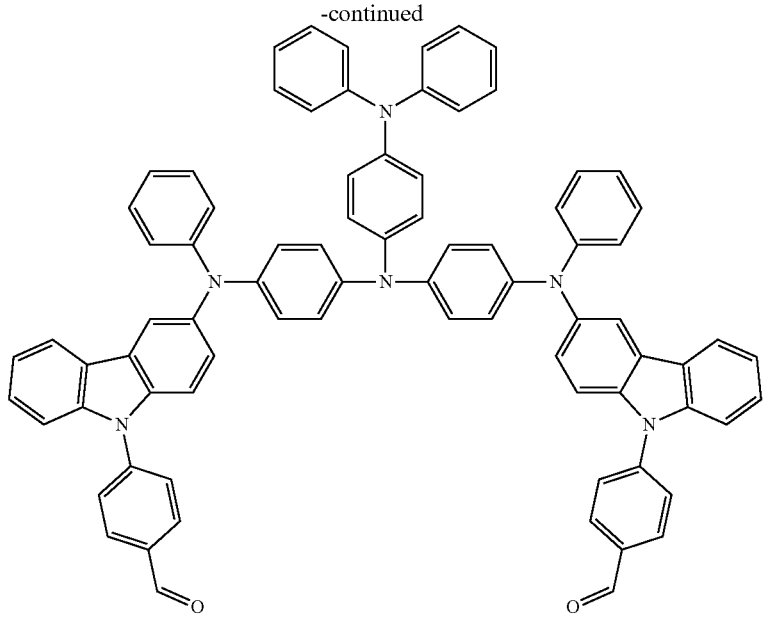
[Chemical Formula D-4-1]
Chemical Formula D-4-1 was obtained in the same manner as in the preparation example of Chemical Formula 1-1-1, except that Chemical Formula C-4-1 was used instead of Chemical Formula C-1-1. MS: [M+H]$^+$=1134
<Preparation of Chemical Formula 1-4-1>
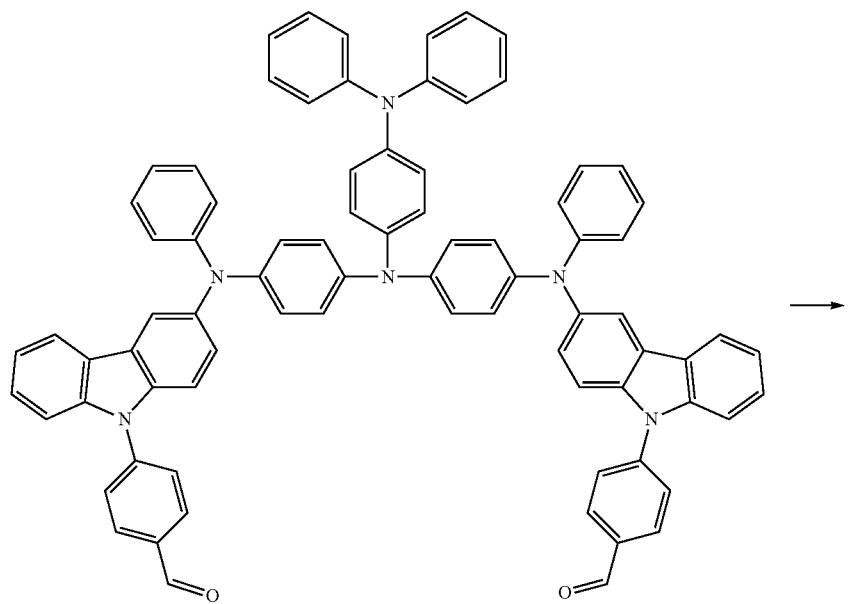
[Chemical Formula D-4-1]

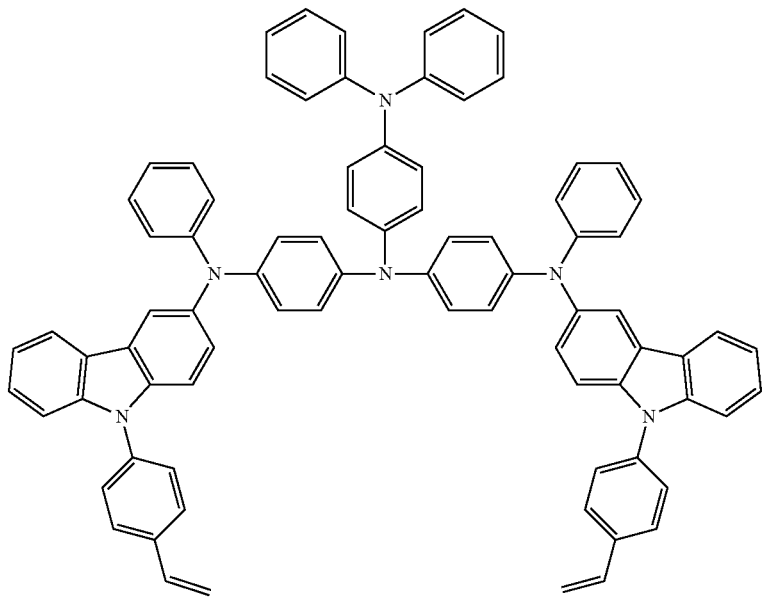
[Chemical Formula 1-4-1]
Chemical Formula 1-4-1 was obtained in the same manner as in the preparation example of Chemical Formula 1-1-1, except that Chemical Formula D-4-1 was used instead of Chemical Formula D-1-1. MS: [M+H]$^+$=1130
Preparation Example 1-5-1. Preparation of Chemical Formula 1-5-1
<Preparation of Chemical Formula D-5-1>
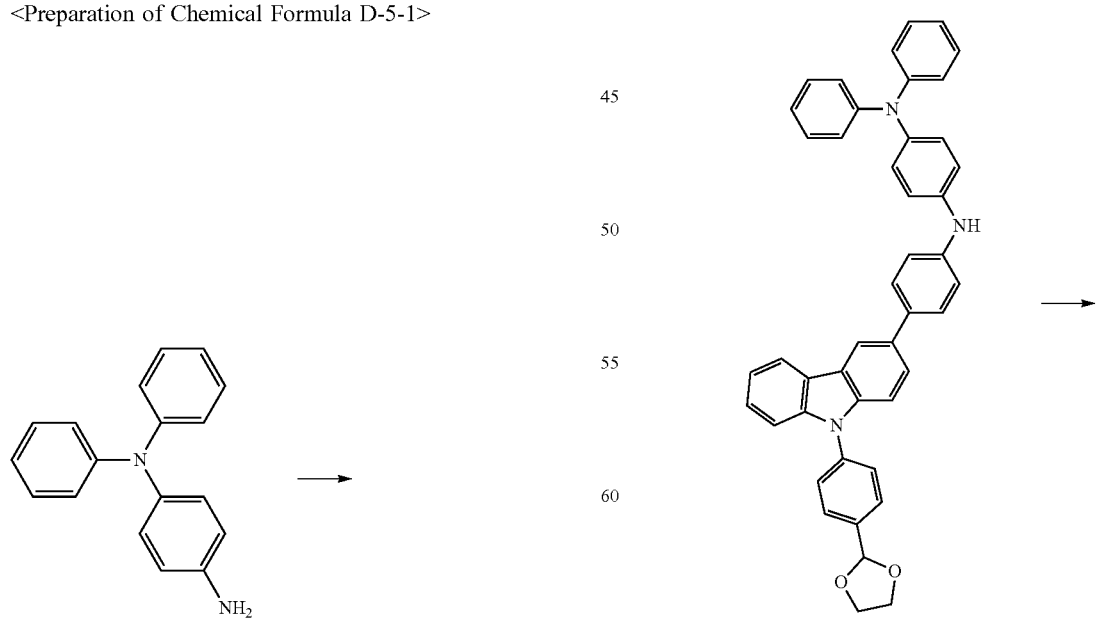
[Chemical Formula B-13]   [Chemical Formula C-5-1]

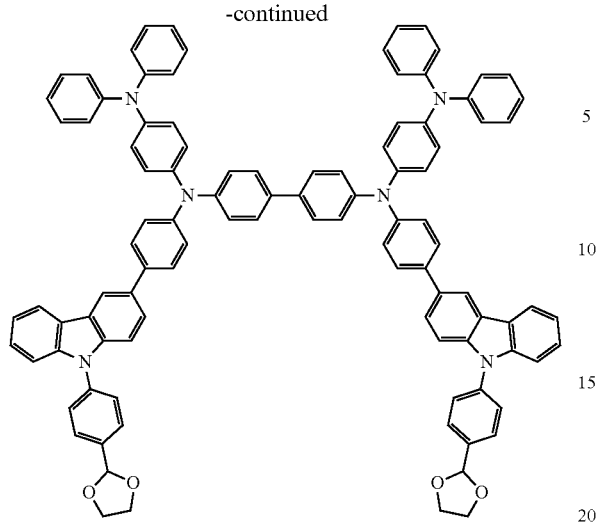

<Preparation of Chemical Formula B-13>

Chemical Formula B-13 was obtained in the same manner as in the preparation example of Chemical Formula B-1 of Chemical Formula 1-1-1, except that Chemical Formula A-2 was used instead of Chemical Formula A-1, and N1,N1-diphenylbenzene-1,4-diamine was used instead of aniline. MS: $[M+H]^+=650$ <Preparation of Chemical Formula C-5-1>

Chemical Formula C-5-1 was obtained in the same manner as in the preparation example of Chemical Formula 1-1-1, except that Chemical Formula B-13 was used instead of Chemical Formula B-1. MS: $[M+H]^+=1450$ <Preparation of Chemical Formula 1-5-1>

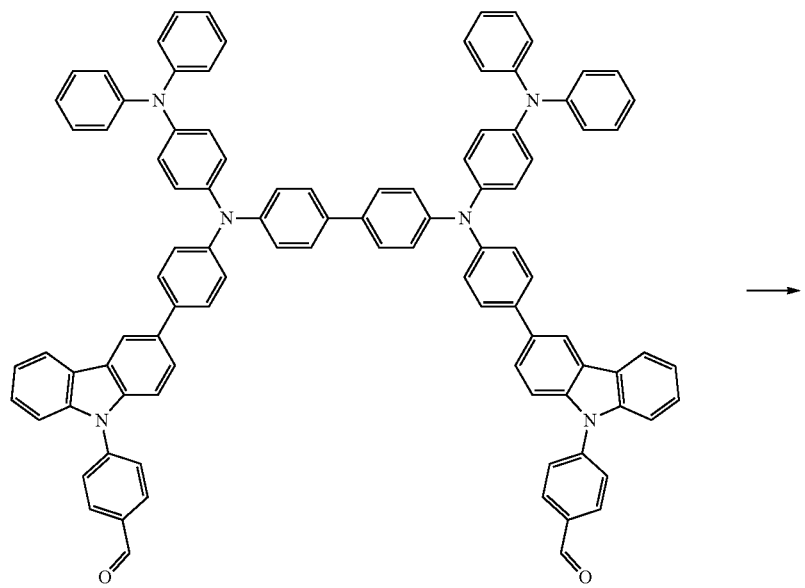

[Chemical Formula D-5-1]

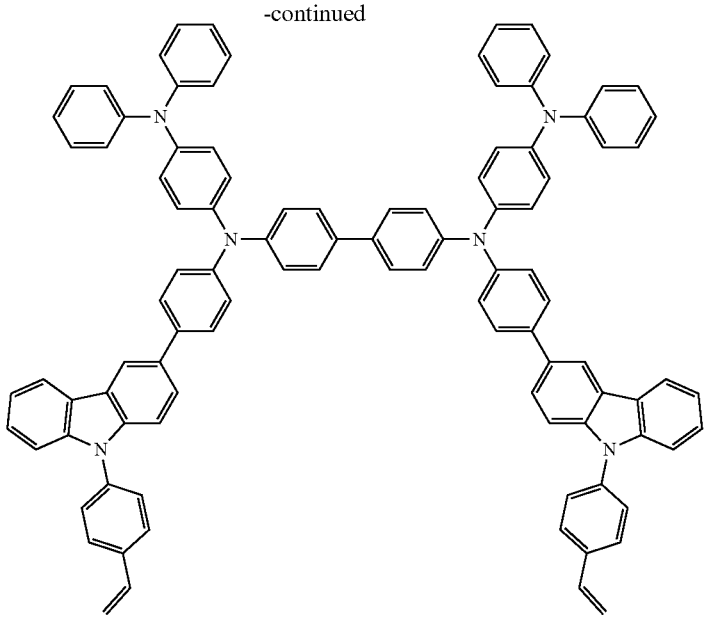

[Chemical Formula 1-5-1]

<Preparation of Chemical Formula D-5-1>

Chemical Formula D-5-1 was obtained in the same manner as in the preparation example of Chemical Formula 1-1-1, except that Chemical Formula C-5-1 was used instead of Chemical Formula C-1-1. MS: $[M+H]^+=1362$ <Preparation of Chemical Formula 1-5-1>

Chemical Formula 1-5-1 was obtained in the same manner as in the preparation example of Chemical Formula 1-1-1, except that Chemical Formula D-5-1 was used instead of Chemical Formula D-1-1. MS: $[M+H]^+=1358$ Test Example 1. Formation of Coating Layer Using Coating Composition As described in the following Table 1-1, a coating composition was produced by mixing the compound represented by Chemical Formula 1 of the present disclosure; a p-doping material; and an organic solvent (cyclohexanone). In addition, the prepared coating composition was spin coated as described in Table 1-1, and the film was baked at a temperature of 250° C. or lower.

As the following p-doping material, an organic compound-type dopant of the following Chemical Formula A, or an ionic dopant of Chemical Formula B was used, however, the p-doping material is not limited thereto.

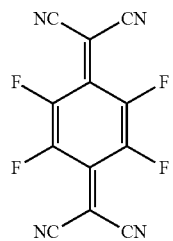

[Chemical Formula A]

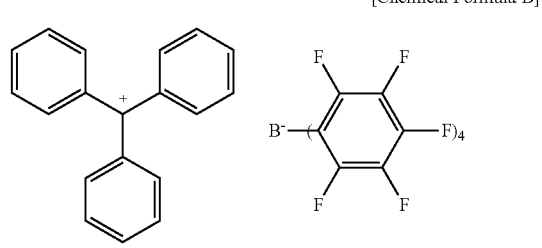

[Chemical Formula B]

TABLE 1

| Coating Composition | Compound (Weight Ratio) | p-Doping Material | Compound:p-Doping Material (Weight Ratio) | Spin Rate (rpm)/ Time (s) | Baking Temperature (° C.)/Time (min) |
|---|---|---|---|---|---|
| 1 | Chemical Formula 1-1-1 | Chemical Formula B | 0.8:0.2 | 1000/60 | 230/30 |
| 2 | Chemical Formula 1-2-1 | Chemical Formula B | 0.8:0.2 | 1000/60 | 230/30 |
| 3 | Chemical Formula 1-3-1 | Chemical Formula A | 0.7:0.3 | 1000/60 | 230/30 |
| 4 | Chemical Formula 1-4-1 | Chemical Formula A | 0.8:0.2 | 1000/60 | 230/30 |
| 5 | Chemical Formula 1-1-1:Chemical Formula 1-2-1 (1:1) | Chemical Formula A | 0.8:0.2 | 1000/60 | 230/30 |
| 6 | Chemical Formula 1-5-1 | Chemical Formula B | 0.8:0.2 | 1000/60 | 230/30 |
| 7 | Chemical Formula 1-1-1:Chemical Formula 1-5-1 (1:1) | Chemical Formula B | 0.8:0.2 | 1000/60 | 230/30 |

Test Example 2. Test on Film Retention Rate of Coating Layer

In order to identify a film retention rate of the coating layer formed using the coating composition of Table 1-1, a toluene solvent was spin treated on the top of the film for washing. It was identified that the films formed using Coating Compositions 1 to 7 included a carbazole derivative including a functional group capable of crosslinking, and had high chemical resistance and film retention rate by the thermocurable group or the photocurable group forming crosslinkage.

Test Example 3. Manufacture of Organic Light Emitting Device

Example 1

A glass substrate on which indium tin oxide (ITO) was coated as a thin film to a thickness of 1,500 Å was placed in detergent-dissolved distilled water and ultrasonic cleaned. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone, then dried, and then transferred to a glove box.

On the transparent ITO electrode prepared as above, Coating Composition 1 described in Table 1-1 was spin coated to form a hole injection layer having a thickness of 300 Å, and the coating composition was cured for 30 minutes on a hot plate under $N_2$ atmosphere. After that, the result was transferred to a vacuum depositor, and then a hole transfer layer was formed by vacuum depositing the following Compound 1 on the hole injection layer.

Compound 1

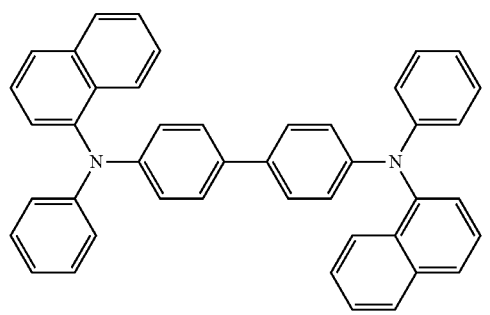

Compound 2

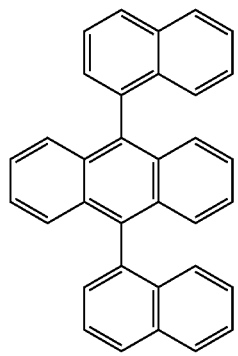

Compound 3

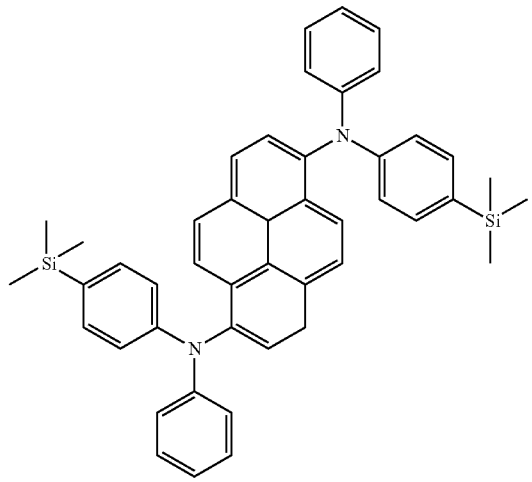

Compound 4

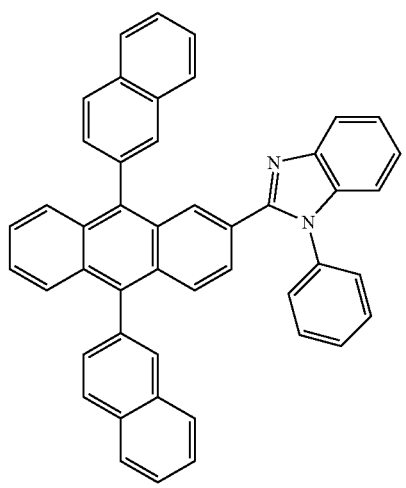

Subsequently, a light emitting layer was formed on the hole transfer layer by vacuum depositing Compound 2 and Compound 3 in 8% concentration to a thickness of 300 Å. An electron injection and transfer layer was formed on the light emitting layer by vacuum depositing Compound 4 to a thickness of 200 Å. A cathode was formed on the electron injection and transfer layer by depositing LiF to a thickness of 12 Å and aluminum to a thickness of 2,000 Å in consecutive order.

In the above process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum was maintained at $2 \times 10^{-7}$ torr to $5 \times 10^{-8}$ torr during the deposition.

Example 2

An organic light emitting device was manufactured in the same manner as in Example 1 except that Coating Composition 2 was used as the hole injection layer instead of Coating Composition 1.

Example 3

An organic light emitting device was manufactured in the same manner as in Example 1 except that Coating Composition 3 was used as the hole injection layer instead of Coating Composition 1.

Example 4

An organic light emitting device was manufactured in the same manner as in Example 1 except that Coating Composition 4 was used as the hole injection layer instead of Coating Composition 1.

Example 5

An organic light emitting device was manufactured in the same manner as in Example 1 except that Coating Composition 5 was used as the hole injection layer instead of Coating Composition 1.

Example 6

An organic light emitting device was manufactured in the same manner as in Example 1 except that Coating Composition 6 was used as the hole injection layer instead of Coating Composition 1.

Example 7

An organic light emitting device was manufactured in the same manner as in Example 1 except that Coating Composition 7 was used as the hole injection layer instead of Coating Composition 1.

Comparative Example 1

An organic light emitting device was manufactured in the same manner as in Example 1 except that PEDOT:PSS was used as the hole injection layer instead of Coating Composition 1.

Results of measuring driving voltage and light emission efficiency of the organic light emitting devices manufactured using the methods described above at current density of 10 $mA/cm^2$ are shown in the following Table 2-1.

TABLE 2

| Example | Driving Voltage (V) | J ($mA/cm^2$) | Current Efficiency (cd/A) |
|---|---|---|---|
| Example 1 | 4.3 | 10 | 4.64 |
| Example 2 | 4.7 | 10 | 4.76 |
| Example 3 | 5.6 | 10 | 3.87 |
| Example 4 | 5.3 | 10 | 4.32 |
| Example 5 | 6.3 | 10 | 2.64 |
| Example 6 | 4.9 | 10 | 4.75 |
| Example 7 | 6.3 | 10 | 3.85 |
| Comparative Example 1 | 5.5 | 10 | 2.11 |

Based on the results of Table 2-1, it was identified that the derivatives of Chemical Formula 1 according to one embodiment of the present specification had excellent solubility for organic solvents, readily prepared a coating composition, and therefore, may form a uniform coating layer using the coating composition, and may be used in an organic light emitting device.

In the examples, functional groups capable of increasing solubility may be preferably introduced to the compounds of Chemical Formula 1 in order to progress with a solution process, and substituents capable of increasing solubility that may be considered by those skilled in the art may be introduced in the present disclosure.

The invention claimed is:
1. A carbazole derivative having any one of the following structural formulae:

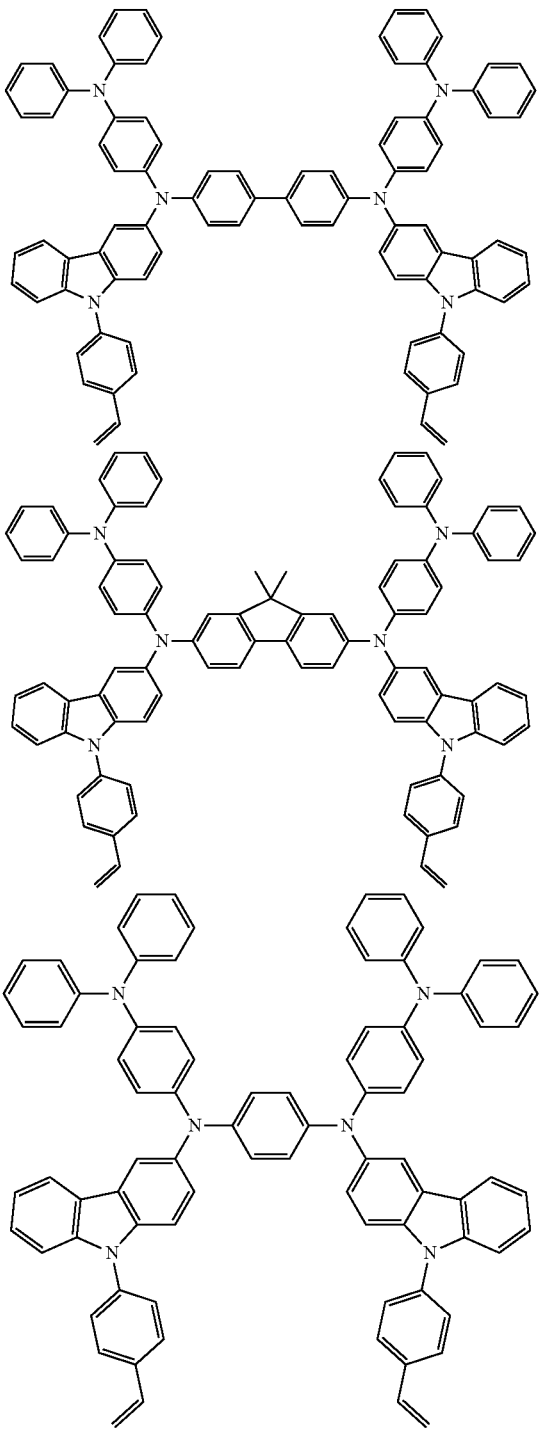

-continued
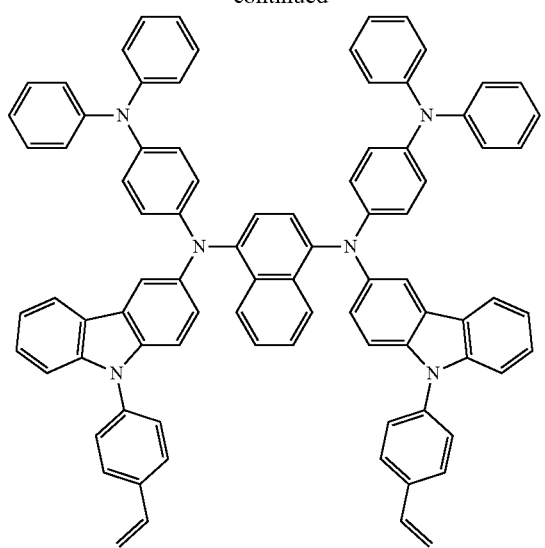
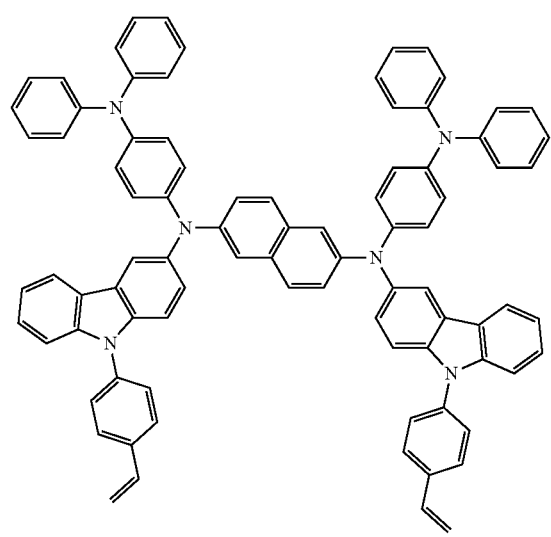
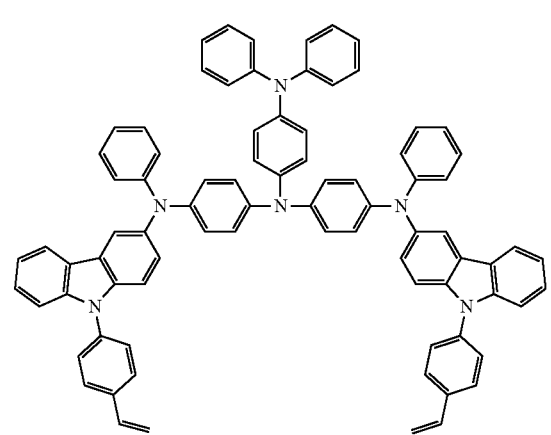
-continued
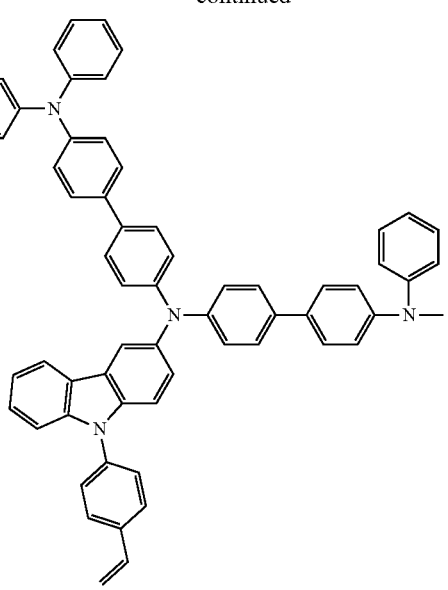
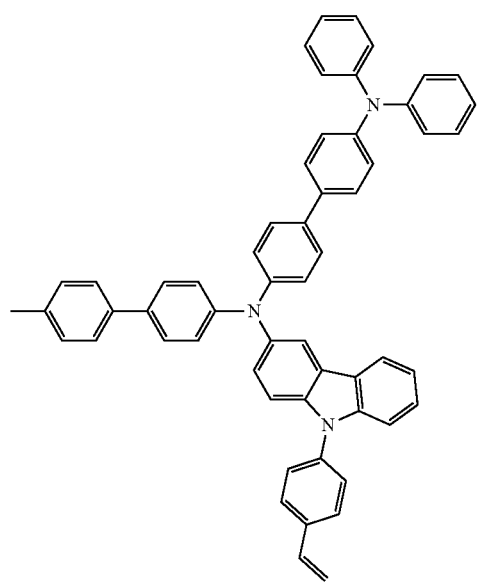
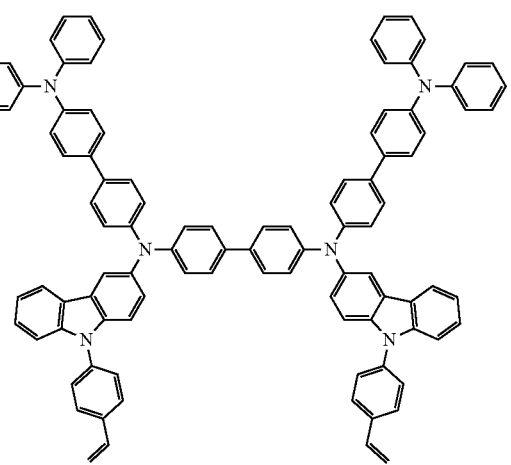

101
-continued
102
-continued
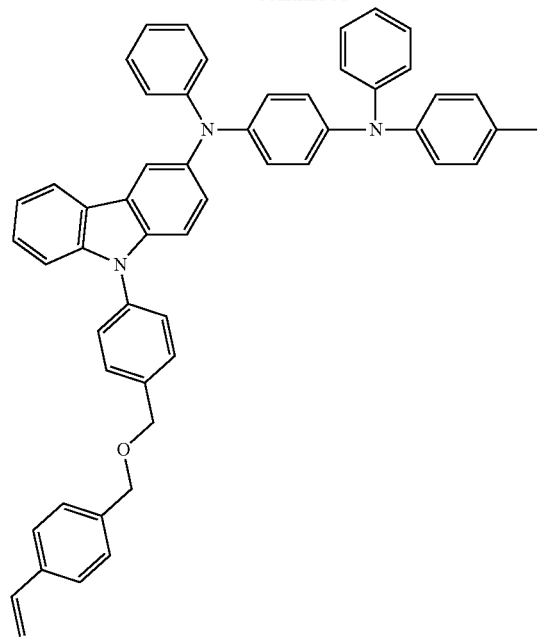
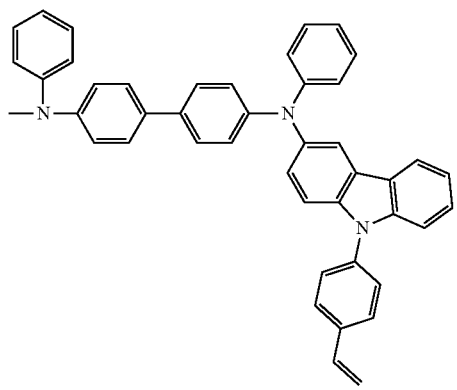
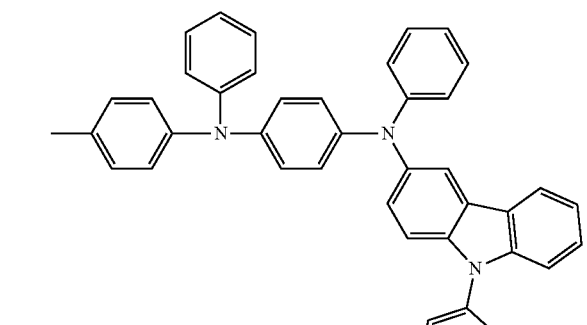
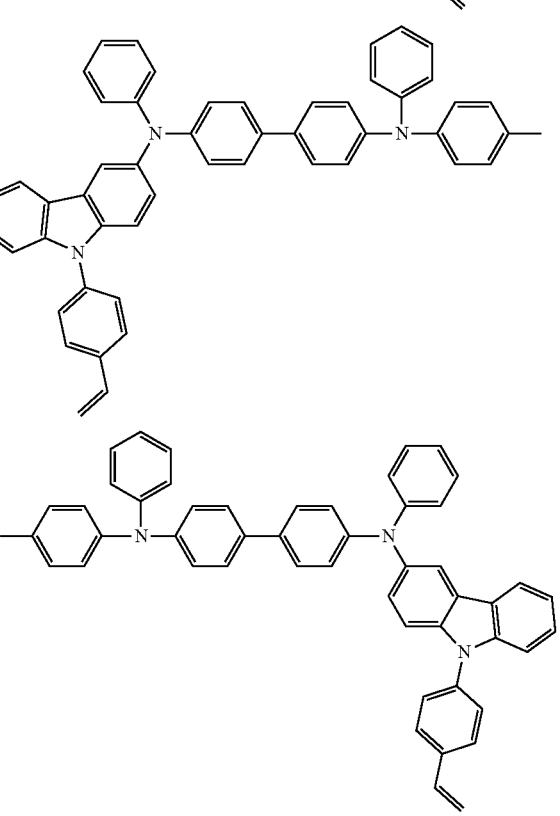
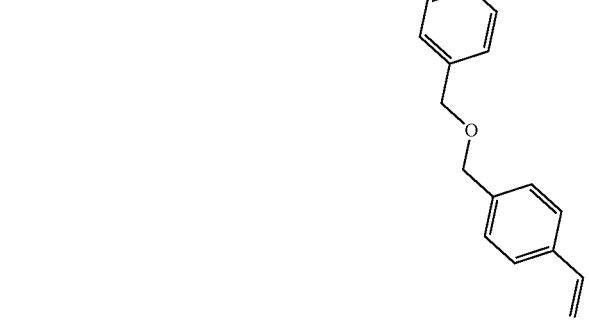
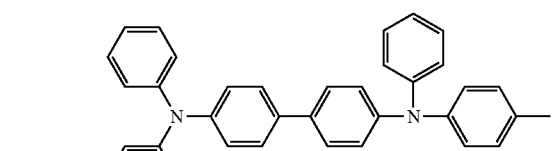
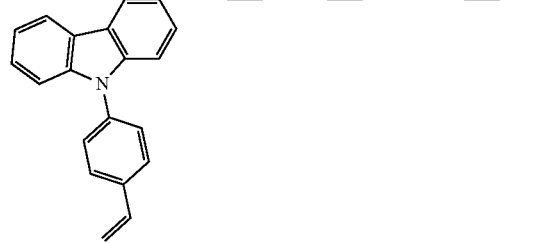

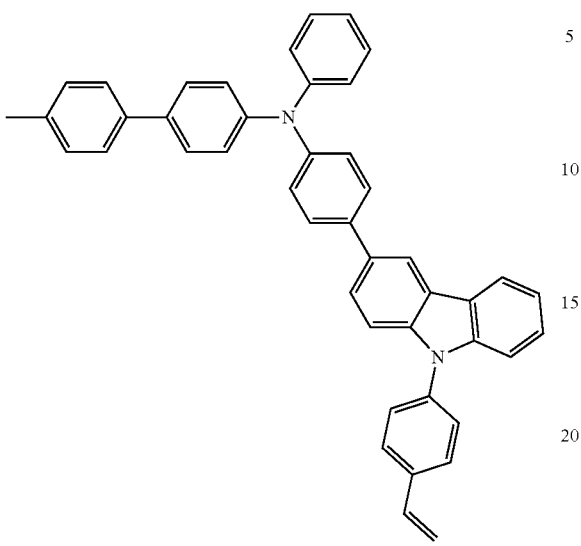

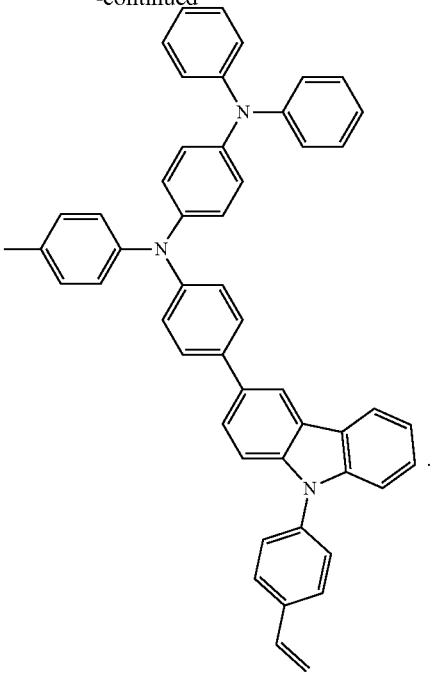

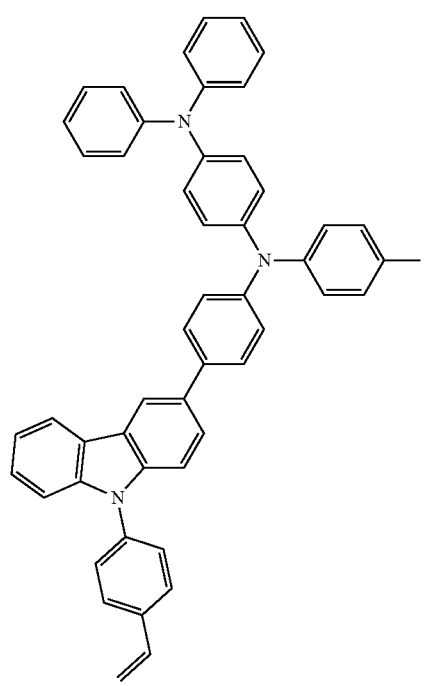

2. A coating composition comprising the carbazole derivative of claim 1.

3. The coating composition of claim 2, further comprising a p-doping material.

4. The coating composition of claim 2, further comprising:
  a monomer comprising a thermocurable group or a photocurable group; or
  a monomer comprising a terminal group capable of forming a polymer by heat.

5. An organic light emitting device comprising:
  a cathode;
  an anode; and
  one or more organic material layers provided between the cathode and the anode,
  wherein one or more layers of the organic material layers comprise a cured material of the coating composition of claim 2.

6. The organic light emitting device of claim 5, wherein the organic material layer comprising a cured material of the coating composition is a hole transfer layer, a hole injection layer, a layer carrying out hole transfer and hole injection at the same time, or a light emitting layer.

7. A method for manufacturing an organic light emitting device comprising:
  preparing a substrate;
  forming a cathode or an anode on the substrate;
  forming one or more organic material layers on the cathode or the anode; and
  forming an anode or a cathode on the organic material layers,
  wherein the forming of organic material layers comprises forming one or more organic material layers using the coating composition of claim 2.

8. The method for manufacturing an organic light emitting device of claim 7, wherein the forming of organic material layers using the coating composition comprises coating the coating composition on the cathode or the anode; and heat treating or light treating the coated coating composition.

* * * * *